(12) United States Patent
Gregorich et al.

(10) Patent No.: US 7,833,266 B2
(45) Date of Patent: Nov. 16, 2010

(54) BIFURCATED STENT WITH DRUG WELLS FOR SPECIFIC OSTIAL, CARINA, AND SIDE BRANCH TREATMENT

(75) Inventors: Daniel Gregorich, St. Louis Park, MN (US); Michael P. Meyer, Richfield, MN (US); David L. Friesen, Otsego, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 246 days.

(21) Appl. No.: 11/946,632

(22) Filed: Nov. 28, 2007

(65) Prior Publication Data

US 2009/0138075 A1    May 28, 2009

(51) Int. Cl.
*A61F 2/06* (2006.01)
(52) U.S. Cl. .................................... 623/1.42; 623/1.35
(58) Field of Classification Search ............... 623/1.35, 623/1.15, 1.39, 1.42–1.46; 606/108, 191–192, 606/194, 198
See application file for complete search history.

(56) References Cited

U.S. PATENT DOCUMENTS

| | | | |
|---|---|---|---|
| 3,948,254 A | 4/1976 | Zaffaroni |
| 4,309,994 A | 1/1982 | Grunwald |
| 4,769,005 A | 9/1988 | Ginsburg et al. |
| 4,774,949 A | 10/1988 | Fogarty |
| 4,784,659 A | 11/1988 | Fleckenstein et al. |
| 4,896,670 A | 1/1990 | Crittenden |
| 4,905,667 A | 3/1990 | Foerster et al. |
| 4,906,244 A | 3/1990 | Pinchuk et al. |
| 4,935,190 A | 6/1990 | Tennerstedt |
| 4,994,071 A | 2/1991 | MacGregor |
| 5,037,392 A | 8/1991 | Hillstead |
| 5,053,007 A | 10/1991 | Euteneuer |
| 5,087,246 A | 2/1992 | Smith |
| 5,112,900 A | 5/1992 | Buddenhagen et al. |
| 5,147,302 A | 9/1992 | Euteneuer et al. |
| 5,163,989 A | 11/1992 | Campbell et al. |
| 5,209,799 A | 5/1993 | Vigil |
| 5,226,887 A | 7/1993 | Farr et al. |
| 5,306,246 A | 4/1994 | Sahatijian et al. |
| 5,318,587 A | 6/1994 | Davey |
| 5,342,307 A | 8/1994 | Euteneuer et al. |
| 5,342,387 A | 8/1994 | Summers |

(Continued)

FOREIGN PATENT DOCUMENTS

CA    2220864    7/1999

(Continued)

OTHER PUBLICATIONS

Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).

(Continued)

*Primary Examiner*—Corrine M McDermott
*Assistant Examiner*—Tiffany Shipmon
(74) *Attorney, Agent, or Firm*—Vidas, Arrett & Steinkraus P.A.

(57) ABSTRACT

The invention is directed to a stent that delivers multiple therapeutic regimens from different regions of the stent.

19 Claims, 6 Drawing Sheets

U.S. PATENT DOCUMENTS

| | | |
|---|---|---|
| 5,348,538 A | 9/1994 | Wang et al. |
| 5,350,361 A | 9/1994 | Tsukashima et al. |
| 5,358,475 A | 10/1994 | Mares et al. |
| 5,387,235 A | 2/1995 | Chuter |
| 5,403,340 A | 4/1995 | Wang et al. |
| 5,447,497 A | 9/1995 | Sogard et al. |
| 5,449,382 A | 9/1995 | Dayton |
| 5,456,666 A | 10/1995 | Campbell et al. |
| 5,456,712 A | 10/1995 | Maginot |
| 5,458,572 A | 10/1995 | Campbell et al. |
| 5,464,650 A | 11/1995 | Berg et al. |
| 5,476,471 A | 12/1995 | Shifrin et al. |
| 5,478,319 A | 12/1995 | Campbell et al. |
| 5,487,730 A | 1/1996 | Marcadis et al. |
| 5,523,092 A | 6/1996 | Hanson et al. |
| 5,549,552 A | 8/1996 | Peters et al. |
| 5,550,180 A | 8/1996 | Elsik et al. |
| 5,556,383 A | 9/1996 | Wang et al. |
| 5,591,228 A | 1/1997 | Edoga |
| 5,605,696 A | 2/1997 | Eury et al. |
| 5,607,444 A | 3/1997 | Lam |
| 5,609,605 A | 3/1997 | Marshall et al. |
| 5,609,627 A | 3/1997 | Goicoechea et al. |
| 5,609,629 A | 3/1997 | Fearnot et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,718,684 A | 2/1998 | Gupta |
| 5,718,724 A | 2/1998 | Goicechea et al. |
| 5,720,735 A | 2/1998 | Dorros |
| 5,746,745 A | 5/1998 | Abele et al. |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,773 A | 5/1998 | Evans et al. |
| 5,755,778 A | 5/1998 | Kleshinski |
| 5,769,884 A * | 6/1998 | Solovay ............... 623/1.13 |
| 5,782,906 A | 7/1998 | Marshall et al. |
| 5,797,898 A | 8/1998 | Santini, Jr. et al. |
| 5,800,520 A | 9/1998 | Fogarty et al. |
| 5,810,767 A | 9/1998 | Klein |
| 5,815,904 A | 10/1998 | Clubb et al. |
| 5,824,036 A | 10/1998 | Lauterjung |
| 5,824,040 A | 10/1998 | Cox et al. |
| 5,827,320 A | 10/1998 | Richter et al. |
| 5,830,182 A | 11/1998 | Wang et al. |
| 5,833,657 A | 11/1998 | Reinhardt et al. |
| 5,843,172 A | 12/1998 | Yan |
| 5,851,464 A | 12/1998 | Davila et al. |
| 5,868,777 A | 2/1999 | Lam |
| 5,882,334 A | 3/1999 | Sepetka et al. |
| 5,891,108 A | 4/1999 | Leone et al. |
| 5,893,887 A | 4/1999 | Jayaraman |
| 5,906,640 A | 5/1999 | Penn et al. |
| 5,922,020 A | 7/1999 | Klein et al. |
| 5,922,021 A | 7/1999 | Jang |
| 5,951,941 A | 9/1999 | Wang et al. |
| 5,961,548 A | 10/1999 | Shmulewitz |
| 5,972,017 A | 10/1999 | Berg et al. |
| 5,972,027 A | 10/1999 | Johnson |
| 5,980,564 A | 11/1999 | Stinson |
| 6,013,054 A | 1/2000 | Jiun Yan |
| 6,013,055 A | 1/2000 | Bampos et al. |
| 6,013,091 A | 1/2000 | Ley et al. |
| 6,017,324 A | 1/2000 | Tu et al. |
| 6,017,363 A | 1/2000 | Hojeibane |
| 6,030,414 A | 2/2000 | Taheri |
| 6,033,380 A | 3/2000 | Butaric et al. |
| 6,033,434 A | 3/2000 | Borghi |
| 6,033,435 A | 3/2000 | Penn et al. |
| 6,048,361 A | 4/2000 | Von Oepen |
| 6,056,775 A | 5/2000 | Borghi et al. |
| 6,059,824 A | 5/2000 | Taheri |
| 6,063,101 A | 5/2000 | Jacobsen et al. |
| 6,068,655 A | 5/2000 | Seguin et al. |
| 6,071,285 A | 6/2000 | Lashinski et al. |
| 6,071,305 A | 6/2000 | Brown et al. |
| 6,086,611 A | 7/2000 | Duffy et al. |
| 6,093,203 A | 7/2000 | Uflacker |
| 6,096,070 A | 8/2000 | Ragheb et al. |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,123,721 A | 9/2000 | Jang |
| 6,126,652 A | 10/2000 | McLeod et al. |
| 6,129,738 A | 10/2000 | Lashinski et al. |
| 6,129,754 A | 10/2000 | Kanesaka et al. |
| 6,135,982 A | 10/2000 | Campbell |
| 6,142,973 A | 11/2000 | Carleton et al. |
| 6,143,002 A | 11/2000 | Vietmeier |
| 6,146,356 A | 11/2000 | Wang et al. |
| 6,159,238 A | 12/2000 | Killion et al. |
| 6,165,195 A | 12/2000 | Wilson et al. |
| 6,168,621 B1 | 1/2001 | Vrba |
| 6,171,278 B1 | 1/2001 | Wang et al. |
| 6,183,509 B1 | 2/2001 | Dibie |
| 6,190,404 B1 | 2/2001 | Palmaz et al. |
| 6,203,568 B1 | 3/2001 | Lombardi et al. |
| 6,206,915 B1 | 3/2001 | Fagan et al. |
| 6,206,916 B1 | 3/2001 | Furst |
| 6,210,380 B1 | 4/2001 | Mauch |
| 6,210,429 B1 | 4/2001 | Vardi et al. |
| 6,210,433 B1 | 4/2001 | Larre |
| 6,210,436 B1 | 4/2001 | Weadock |
| 6,214,042 B1 | 4/2001 | Jacobsen et al. |
| 6,231,598 B1 | 5/2001 | Berry et al. |
| 6,240,616 B1 | 6/2001 | Yan |
| 6,241,762 B1 | 6/2001 | Shanley |
| 6,253,443 B1 | 7/2001 | Johnson |
| 6,254,593 B1 | 7/2001 | Wilson |
| 6,254,632 B1 | 7/2001 | Wu et al. |
| 6,258,115 B1 | 7/2001 | Dubrul |
| 6,258,116 B1 | 7/2001 | Hojeibane |
| 6,258,121 B1 | 7/2001 | Yang et al. |
| 6,261,305 B1 | 7/2001 | Marotta et al. |
| 6,261,316 B1 | 7/2001 | Shaolian et al. |
| 6,261,320 B1 | 7/2001 | Tam et al. |
| 6,264,662 B1 | 7/2001 | Lauterjung |
| 6,264,686 B1 | 7/2001 | Rieu et al. |
| 6,273,908 B1 | 8/2001 | Ndondo-Lay |
| 6,273,913 B1 | 8/2001 | Wright et al. |
| 6,280,413 B1 | 8/2001 | Clark et al. |
| 6,287,628 B1 | 9/2001 | Hossainy et al. |
| 6,290,673 B1 | 9/2001 | Shanley |
| 6,293,967 B1 | 9/2001 | Shanley |
| 6,293,968 B1 | 9/2001 | Taheri |
| 6,299,604 B1 * | 10/2001 | Ragheb et al. ............... 604/265 |
| 6,325,825 B1 | 12/2001 | Kula et al. |
| 6,325,826 B1 | 12/2001 | Vardi et al. |
| 6,328,925 B1 | 12/2001 | Wang et al. |

| | | | | | | |
|---|---|---|---|---|---|---|
| 6,334,864 B1 | 1/2002 | Amplatz et al. | | 6,783,543 B2 | 8/2004 | Jang |
| 6,334,870 B1 | 1/2002 | Ehr et al. | | 6,790,228 B2 | 9/2004 | Hossainy et al. |
| 6,346,089 B1 | 2/2002 | Dibie | | 6,805,898 B1 | 10/2004 | Wu et al. |
| 6,348,065 B1 | 2/2002 | Brown et al. | | 6,811,566 B1 | 11/2004 | Penn et al. |
| 6,355,060 B1 | 3/2002 | Lenker et al. | | 6,815,609 B1 | 11/2004 | Wang et al. |
| 6,358,552 B1 | 3/2002 | Mandralis et al. | | 6,827,250 B2 | 12/2004 | Uhland et al. |
| 6,361,544 B1 | 3/2002 | Wilson et al. | | 6,835,203 B1 | 12/2004 | Vardi et al. |
| 6,361,555 B1 | 3/2002 | Wilson | | 6,846,323 B2 | 1/2005 | Yip et al. |
| 6,379,381 B1 | 4/2002 | Hossainy et al. | | 6,858,038 B2 | 2/2005 | Heuser |
| 6,379,382 B1 | 4/2002 | Yang | | 6,875,227 B2 | 4/2005 | Yoon |
| 6,383,213 B2 | 5/2002 | Wilson et al. | | 6,884,258 B2 | 4/2005 | Vardi et al. |
| 6,395,018 B1 | 5/2002 | Castaneda | | 6,884,429 B2 | 4/2005 | Koziak et al. |
| 6,395,326 B1 | 5/2002 | Castro et al. | | 6,896,697 B1 | 5/2005 | Yip et al. |
| 6,406,457 B1 | 6/2002 | Wang et al. | | 6,896,699 B2 | 5/2005 | Wilson et al. |
| 6,423,091 B1 | 7/2002 | Hojeibane | | 6,904,658 B2 | 6/2005 | Hines |
| 6,436,104 B2 | 8/2002 | Hojeibane | | 6,913,617 B1 | 7/2005 | Reiss |
| 6,436,134 B2 | 8/2002 | Richter et al. | | 6,918,927 B2 | 7/2005 | Bates et al. |
| 6,471,721 B1 | 10/2002 | Dang | | 6,932,837 B2 | 8/2005 | Amplatz et al. |
| 6,471,980 B2 | 10/2002 | Sirhan et al. | | 6,946,092 B1 | 9/2005 | Bertolino et al. |
| 6,478,816 B1 | 11/2002 | Kveen et al. | | 6,955,685 B2 | 10/2005 | Escamilla et al. |
| 6,491,666 B1 | 12/2002 | Santini, Jr. et al. | | 6,955,687 B2 | 10/2005 | Richter et al. |
| 6,506,437 B1 | 1/2003 | Harish et al. | | 6,955,688 B2 | 10/2005 | Wilson et al. |
| 6,508,836 B2 | 1/2003 | Wilson et al. | | 6,962,602 B2 | 11/2005 | Vardi et al. |
| 6,517,558 B2 | 2/2003 | Gittings et al. | | 6,962,822 B2 | 11/2005 | Hart et al. |
| 6,517,858 B1 | 2/2003 | Le Moel et al. | | 6,973,718 B2 | 12/2005 | Sheppard, Jr. et al. |
| 6,520,988 B1 | 2/2003 | Colombo et al. | | 6,979,347 B1 | 12/2005 | Wu et al. |
| 6,521,284 B1 | 2/2003 | Parsons et al. | | 6,989,071 B2 | 1/2006 | Kocur et al. |
| 6,527,762 B1 | 3/2003 | Santini, Jr. et al. | | D516,723 S | 3/2006 | Shanley |
| 6,527,799 B2 | 3/2003 | Shanley | | 7,018,400 B2 | 3/2006 | Lashinski et al. |
| 6,527,938 B2 | 3/2003 | Bales et al. | | 7,041,130 B2 | 5/2006 | Santini, Jr. et al. |
| 6,537,256 B2 | 3/2003 | Santini, Jr. et al. | | 7,044,965 B1 | 5/2006 | Spielberg |
| 6,540,779 B2 | 4/2003 | Richter et al. | | 7,052,488 B2 | 5/2006 | Uhland |
| 6,544,582 B1 | 4/2003 | Yoe | | 7,056,323 B2 | 6/2006 | Mareiro et al. |
| 6,551,351 B2 | 4/2003 | Smith et al. | | 7,056,338 B2 | 6/2006 | Shanley et al. |
| 6,551,838 B2 | 4/2003 | Santini, Jr. et al. | | 7,060,091 B2 | 6/2006 | Killion et al. |
| 6,558,422 B1 | 5/2003 | Baker et al. | | 7,070,616 B2 | 7/2006 | Majercak et al. |
| 6,558,733 B1 | 5/2003 | Hossainy et al. | | 7,105,018 B1 | 9/2006 | Yip et al. |
| 6,562,065 B1 | 5/2003 | Shanley | | 7,114,312 B2 | 10/2006 | Coppeta et al. |
| 6,579,309 B1 | 6/2003 | Loos et al. | | 7,135,038 B1 | 11/2006 | Limon |
| 6,579,312 B2 | 6/2003 | Wilson et al. | | 7,160,321 B2 | 1/2007 | Shanley |
| 6,582,394 B1 | 6/2003 | Reiss et al. | | 7,163,715 B1 | 1/2007 | Kramer |
| 6,585,765 B1 | 7/2003 | Hossainy et al. | | 7,169,175 B2 | 1/2007 | Cottone, Jr. et al. |
| 6,596,020 B2 | 7/2003 | Vardi et al. | | 7,169,178 B1 | 1/2007 | Santos et al. |
| 6,599,316 B2 | 7/2003 | Vardi et al. | | 7,169,179 B2 | 1/2007 | Shanley et al. |
| 6,635,082 B1 | 10/2003 | Hossainy et al. | | 7,179,288 B2 | 2/2007 | Shanley |
| 6,638,302 B1 | 10/2003 | Curcio et al. | | 7,179,289 B2 | 2/2007 | Shanley |
| 6,641,607 B1 | 11/2003 | Hossainy et al. | | 7,208,010 B2 | 4/2007 | Shanley et al. |
| 6,645,242 B1 | 11/2003 | Quinn | | 7,208,011 B2 | 4/2007 | Shanley et al. |
| 6,652,581 B1 | 11/2003 | Ding | | 7,220,275 B2 | 5/2007 | Davidson et al. |
| 6,656,162 B2 | 12/2003 | Santini, Jr. et al. | | 7,223,282 B1 | 5/2007 | Hossainy |
| 6,660,034 B1 | 12/2003 | Mandrusov et al. | | 7,229,413 B2 | 6/2007 | Violante et al. |
| 6,663,664 B1 | 12/2003 | Pacetti | | 7,229,471 B2 | 6/2007 | Gale et al. |
| 6,669,683 B2 | 12/2003 | Santini, Jr. et al. | | 7,238,199 B2 | 7/2007 | Feldman et al. |
| 6,689,156 B1 | 2/2004 | Davidson et al. | | 7,244,442 B2 | 7/2007 | Williams et al. |
| 6,692,483 B2 | 2/2004 | Vardi et al. | | 7,309,353 B2 | 12/2007 | Krivoruchko |
| 6,695,877 B2 | 2/2004 | Brucker et al. | | 7,316,710 B1 | 1/2008 | Cheng et al. |
| 6,706,062 B2 | 3/2004 | Vardi et al. | | 7,335,314 B2 | 2/2008 | Wu et al. |
| 6,709,379 B1 | 3/2004 | Brandau et al. | | 7,393,359 B2 | 7/2008 | Verin et al. |
| 6,709,451 B1 | 3/2004 | Noble et al. | | 7,410,498 B2 | 8/2008 | Penhasi |
| 6,713,119 B2 | 3/2004 | Hossainy et al. | | 7,413,846 B2 | 8/2008 | Maloney et al. |
| 6,716,444 B1 | 4/2004 | Castro et al. | | 7,416,559 B2 | 8/2008 | Shalaby |
| 6,725,901 B1 | 4/2004 | Kramer et al. | | 7,425,217 B2 | 9/2008 | Maier et al. |
| 6,730,064 B2 | 5/2004 | Ragheb et al. | | 7,455,753 B2 | 11/2008 | Roth |
| 6,730,120 B2 | 5/2004 | Berg et al. | | 2001/0003161 A1 | 6/2001 | Vardi et al. |
| 6,749,628 B1 | 6/2004 | Callol et al. | | 2001/0004706 A1 | 6/2001 | Hojeibane |
| 6,752,826 B2 | 6/2004 | Holloway et al. | | 2001/0004707 A1 | 6/2001 | Dereume et al. |
| 6,753,071 B1 | 6/2004 | Pacetti | | 2001/0012927 A1 | 8/2001 | Mauch |
| 6,758,859 B1 | 7/2004 | Dang et al. | | 2001/0016766 A1 | 8/2001 | Vardi et al. |
| 6,764,505 B1 | 7/2004 | Hossainy et al. | | 2001/0016767 A1 | 8/2001 | Wilson et al. |
| 6,764,507 B2 | 7/2004 | Shanley et al. | | 2001/0016768 A1 | 8/2001 | Wilson et al. |
| 6,773,429 B2 | 8/2004 | Sheppard, Jr. et al. | | 2001/0025195 A1 | 9/2001 | Shaolian et al. |
| 6,776,793 B2 | 8/2004 | Brown et al. | | 2001/0027291 A1 | 10/2001 | Shanley |
| 6,780,424 B2 | 8/2004 | Claude | | 2001/0027338 A1 | 10/2001 | Greenberg |

| | | | | | | |
|---|---|---|---|---|---|---|
| 2001/0029396 A1 | 10/2001 | Wilson et al. | | 2004/0088007 A1 | 5/2004 | Eidenschink |
| 2001/0029660 A1* | 10/2001 | Johnson ............... 29/557 | | 2004/0088038 A1 | 5/2004 | Dehnad et al. |
| 2001/0037116 A1 | 11/2001 | Wilson et al. | | 2004/0093071 A1 | 5/2004 | Jang |
| 2001/0037138 A1 | 11/2001 | Wilson et al. | | 2004/0093076 A1 | 5/2004 | White et al. |
| 2001/0039448 A1 | 11/2001 | Dibie | | 2004/0098089 A1 | 5/2004 | Weber |
| 2001/0049552 A1 | 12/2001 | Richter et al. | | 2004/0117003 A1 | 6/2004 | Ouriel et al. |
| 2001/0056297 A1 | 12/2001 | Hojeibane | | 2004/0117008 A1 | 6/2004 | Wnendt et al. |
| 2002/0013618 A1 | 1/2002 | Marotta et al. | | 2004/0122505 A1 | 6/2004 | Shanley |
| 2002/0013619 A1 | 1/2002 | Shanley | | 2004/0122506 A1 | 6/2004 | Shanley et al. |
| 2002/0022874 A1 | 2/2002 | Wilson | | 2004/0127976 A1 | 7/2004 | Diaz |
| 2002/0026232 A1 | 2/2002 | Marotta et al. | | 2004/0127977 A1 | 7/2004 | Shanley |
| 2002/0035392 A1 | 3/2002 | Wilson | | 2004/0133268 A1 | 7/2004 | Davidson et al. |
| 2002/0038146 A1 | 3/2002 | Harry | | 2004/0133270 A1 | 7/2004 | Grandt |
| 2002/0042650 A1 | 4/2002 | Vardi et al. | | 2004/0138732 A1 | 7/2004 | Suhr et al. |
| 2002/0052648 A1 | 5/2002 | McGuckin, Jr. et al. | | 2004/0138737 A1* | 7/2004 | Davidson et al. ............ 623/1.35 |
| 2002/0072790 A1 | 6/2002 | McGuckin, Jr. et al. | | 2004/0142014 A1 | 7/2004 | Litvack et al. |
| 2002/0095208 A1 | 7/2002 | Gregorich et al. | | 2004/0143321 A1 | 7/2004 | Litvack et al. |
| 2002/0103527 A1 | 8/2002 | Kocur et al. | | 2004/0143322 A1 | 7/2004 | Livack et al. |
| 2002/0103528 A1 | 8/2002 | Schaldach et al. | | 2004/0148006 A1 | 7/2004 | Davidson et al. |
| 2002/0111675 A1 | 8/2002 | Wilson | | 2004/0148010 A1 | 7/2004 | Rush |
| 2002/0120326 A1 | 8/2002 | Michal | | 2004/0148012 A9 | 7/2004 | Jang |
| 2002/0123801 A1 | 9/2002 | Pacetti et al. | | 2004/0167572 A1 | 8/2004 | Roth et al. |
| 2002/0138136 A1 | 9/2002 | Chandresekaran et al. | | 2004/0172121 A1 | 9/2004 | Eidenschink et al. |
| 2002/0155212 A1 | 10/2002 | Hossainy | | 2004/0186560 A1 | 9/2004 | Alt |
| 2002/0156516 A1 | 10/2002 | Vardi et al. | | 2004/0202692 A1 | 10/2004 | Shanley et al. |
| 2002/0156517 A1 | 10/2002 | Perouse | | 2004/0204750 A1 | 10/2004 | Dinh |
| 2002/0163104 A1 | 11/2002 | Motsenbocker et al. | | 2004/0211362 A1 | 10/2004 | Castro et al. |
| 2002/0165604 A1 | 11/2002 | Shanley | | 2004/0215227 A1 | 10/2004 | McMorrow et al. |
| 2002/0173835 A1 | 11/2002 | Bourang et al. | | 2004/0220661 A1 | 11/2004 | Shanley et al. |
| 2002/0173840 A1 | 11/2002 | Brucker et al. | | 2004/0225345 A1 | 11/2004 | Fischell et al. |
| 2002/0183721 A1 | 12/2002 | Santini et al. | | 2004/0236408 A1 | 11/2004 | Shanley |
| 2002/0183763 A1 | 12/2002 | Callol et al. | | 2004/0236416 A1 | 11/2004 | Falotico |
| 2002/0193336 A1 | 12/2002 | Elkins et al. | | 2004/0237282 A1 | 12/2004 | Hines |
| 2002/0193872 A1 | 12/2002 | Trout, III et al. | | 2004/0247671 A1 | 12/2004 | Prescott et al. |
| 2002/0193873 A1 | 12/2002 | Brucker et al. | | 2004/0249449 A1 | 12/2004 | Shanley et al. |
| 2003/0009209 A1 | 1/2003 | Hojeibane | | 2004/0267352 A1 | 12/2004 | Davidson et al. |
| 2003/0028233 A1 | 2/2003 | Vardi et al. | | 2005/0004656 A1 | 1/2005 | Das |
| 2003/0032892 A1 | 2/2003 | Erlach et al. | | 2005/0010278 A1 | 1/2005 | Vardi et al. |
| 2003/0050688 A1 | 3/2003 | Fischell et al. | | 2005/0015108 A1 | 1/2005 | Williams et al. |
| 2003/0055378 A1 | 3/2003 | Wang et al. | | 2005/0015135 A1 | 1/2005 | Shanley |
| 2003/0055483 A1 | 3/2003 | Gumm | | 2005/0015142 A1 | 1/2005 | Austin et al. |
| 2003/0060871 A1 | 3/2003 | Hill et al. | | 2005/0021127 A1 | 1/2005 | Kawula |
| 2003/0064095 A1 | 4/2003 | Martin et al. | | 2005/0027350 A1 | 2/2005 | Momma et al. |
| 2003/0069631 A1 | 4/2003 | Stoll | | 2005/0033417 A1 | 2/2005 | Borges et al. |
| 2003/0074047 A1 | 4/2003 | Richter | | 2005/0043816 A1 | 2/2005 | Datta et al. |
| 2003/0083687 A1 | 5/2003 | Pallazza | | 2005/0055080 A1 | 3/2005 | Istephanous et al. |
| 2003/0088312 A1 | 5/2003 | Kopia et al. | | 2005/0060020 A1 | 3/2005 | Jensen |
| 2003/0093109 A1 | 5/2003 | Mauch | | 2005/0060021 A1 | 3/2005 | O'Brien et al. |
| 2003/0097169 A1 | 5/2003 | Brucker | | 2005/0060027 A1 | 3/2005 | Khenansho et al. |
| 2003/0104590 A1 | 6/2003 | Santini, Jr. et al. | | 2005/0074545 A1 | 4/2005 | Thomas |
| 2003/0105511 A1 | 6/2003 | Welsh et al. | | 2005/0079199 A1 | 4/2005 | Heruth et al. |
| 2003/0105512 A1* | 6/2003 | Kanesaka ................ 623/1.15 | | 2005/0095267 A1 | 5/2005 | Campbell et al. |
| 2003/0114912 A1 | 6/2003 | Sequin et al. | | 2005/0096726 A1 | 5/2005 | Sequin et al. |
| 2003/0125791 A1 | 7/2003 | Sequin et al. | | 2005/0102017 A1 | 5/2005 | Mattison |
| 2003/0125802 A1 | 7/2003 | Callol et al. | | 2005/0102021 A1 | 5/2005 | Osborne |
| 2003/0135259 A1 | 7/2003 | Simso | | 2005/0102023 A1 | 5/2005 | Yadin et al. |
| 2003/0139801 A1* | 7/2003 | Sirhan et al. ............... 623/1.15 | | 2005/0106212 A1 | 5/2005 | Gertner et al. |
| 2003/0153901 A1 | 8/2003 | Herweck et al. | | 2005/0119723 A1 | 6/2005 | Peacock |
| 2003/0163157 A1 | 8/2003 | McMorrow et al. | | 2005/0119731 A1 | 6/2005 | Brucker et al. |
| 2003/0167085 A1 | 9/2003 | Shanley | | 2005/0125076 A1 | 6/2005 | Ginn |
| 2003/0181923 A1 | 9/2003 | Vardi | | 2005/0131526 A1 | 6/2005 | Wong |
| 2003/0195606 A1 | 10/2003 | Davidson et al. | | 2005/0136090 A1 | 6/2005 | Falotico et al. |
| 2003/0199970 A1 | 10/2003 | Shanley | | 2005/0137677 A1 | 6/2005 | Rush |
| 2003/0216803 A1 | 11/2003 | Ledergerber | | 2005/0137679 A1 | 6/2005 | Changelian et al. |
| 2004/0000540 A1 | 1/2004 | Soboyejo et al. | | 2005/0137684 A1 | 6/2005 | Changelian et al. |
| 2004/0006381 A1 | 1/2004 | Sequin et al. | | 2005/0149161 A1 | 7/2005 | Eidenschink et al. |
| 2004/0015227 A1 | 1/2004 | Vardi et al. | | 2005/0154442 A1 | 7/2005 | Eidenschink et al. |
| 2004/0034337 A1 | 2/2004 | Boulais et al. | | 2005/0154444 A1 | 7/2005 | Quadri |
| 2004/0043042 A1 | 3/2004 | Johnson et al. | | 2005/0159805 A1 | 7/2005 | Weber et al. |
| 2004/0044396 A1 | 3/2004 | Clerc et al. | | 2005/0171595 A1 | 8/2005 | Feldman et al. |
| 2004/0059406 A1 | 3/2004 | Cully et al. | | 2005/0183259 A1 | 8/2005 | Eidenschink et al. |
| 2004/0068161 A1 | 4/2004 | Couvillon, Jr. | | 2005/0187602 A1 | 8/2005 | Eidenschink |
| 2004/0073294 A1 | 4/2004 | Diaz et al. | | 2005/0187611 A1 | 8/2005 | Ding et al. |

| | | |
|---|---|---|
| 2005/0192657 A1 | 9/2005 | Colen et al. |
| 2005/0196424 A1 | 9/2005 | Chappa |
| 2005/0208100 A1 | 9/2005 | Weber et al. |
| 2005/0209673 A1 | 9/2005 | Shaked |
| 2005/0209681 A1 | 9/2005 | Curcio et al. |
| 2005/0222668 A1 | 10/2005 | Schaeffer et al. |
| 2005/0228477 A1 | 10/2005 | Grainger et al. |
| 2005/0228483 A1 | 10/2005 | Kaplan et al. |
| 2005/0228491 A1 | 10/2005 | Snyder et al. |
| 2005/0232968 A1 | 10/2005 | Palmaz et al. |
| 2005/0234538 A1 | 10/2005 | Litvack et al. |
| 2005/0251245 A1 | 11/2005 | Sieradzik et al. |
| 2005/0256564 A1 | 11/2005 | Yang et al. |
| 2005/0261757 A1 | 11/2005 | Shanley |
| 2005/0266039 A1 | 12/2005 | Weber |
| 2005/0266040 A1 | 12/2005 | Gerberding |
| 2005/0271696 A1 | 12/2005 | Dinn et al. |
| 2005/0273149 A1 | 12/2005 | Tran et al. |
| 2005/0278929 A1 | 12/2005 | Lee |
| 2005/0283225 A1 | 12/2005 | Klisch |
| 2005/0287287 A1 | 12/2005 | Parker et al. |
| 2006/0015134 A1 | 1/2006 | Trinidad |
| 2006/0025848 A1 | 2/2006 | Weber et al. |
| 2006/0034884 A1 | 2/2006 | Stenzel |
| 2006/0036315 A1 | 2/2006 | Yadin et al. |
| 2006/0041303 A1 | 2/2006 | Israel |
| 2006/0045901 A1 | 3/2006 | Weber |
| 2006/0052744 A1 | 3/2006 | Weber |
| 2006/0053618 A1 | 3/2006 | Verin et al. |
| 2006/0069427 A1 | 3/2006 | Savaget et al. |
| 2006/0079956 A1 | 4/2006 | Eigler et al. |
| 2006/0085065 A1 | 4/2006 | Krause et al. |
| 2006/0088654 A1 | 4/2006 | Ding et al. |
| 2006/0093643 A1 | 5/2006 | Stenzel |
| 2006/0100608 A1 | 5/2006 | Uhland et al. |
| 2006/0100686 A1 | 5/2006 | Bolduc |
| 2006/0122698 A1 | 6/2006 | Spencer et al. |
| 2006/0129215 A1 | 6/2006 | Helmus et al. |
| 2006/0129225 A1 | 6/2006 | Kopia |
| 2006/0136051 A1 | 6/2006 | Furst et al. |
| 2006/0161264 A1 | 7/2006 | Ferreyrol |
| 2006/0171989 A1 | 8/2006 | Prescott et al. |
| 2006/0173528 A1 | 8/2006 | Feld et al. |
| 2006/0198750 A1 | 9/2006 | Furst et al. |
| 2006/0200229 A1 | 9/2006 | Bugermeister et al. |
| 2006/0206188 A1 | 9/2006 | Weber et al. |
| 2006/0217801 A1 | 9/2006 | Rosenthal |
| 2006/0224234 A1 | 10/2006 | Jayaraman |
| 2006/0224237 A1 | 10/2006 | Furst et al. |
| 2006/0229713 A1 | 10/2006 | Shanley |
| 2006/0235504 A1 | 10/2006 | Gonzales |
| 2006/0259005 A1 | 11/2006 | Konstantino et al. |
| 2006/0269475 A1 | 11/2006 | Ryu et al. |
| 2006/0275341 A1 | 12/2006 | Liv et al. |
| 2006/0287712 A1 | 12/2006 | Eidenschink |
| 2007/0005126 A1 | 1/2007 | Tischler |
| 2007/0027530 A1 | 2/2007 | Saint et al. |
| 2007/0032430 A1 | 2/2007 | Fogelman et al. |
| 2007/0038176 A1 | 2/2007 | Weber et al. |
| 2007/0043423 A1 | 2/2007 | Grewe |
| 2007/0050016 A1 | 3/2007 | Gregorich et al. |
| 2007/0055352 A1 | 3/2007 | Naimark et al. |
| 2007/0065418 A1 | 3/2007 | Vallana |
| 2007/0065477 A1 | 3/2007 | Parker et al. |
| 2007/0073376 A1 | 3/2007 | Krolik et al. |
| 2007/0073384 A1 | 3/2007 | Brown et al. |
| 2007/0073385 A1 | 3/2007 | Schaeffer et al. |
| 2007/0100434 A1 | 5/2007 | Gregorich et al. |
| 2007/0100438 A1 | 5/2007 | Civelli |
| 2007/0110786 A1 | 5/2007 | Tenney |
| 2007/0112888 A1 | 5/2007 | Radhakrishnan et al. |
| 2007/0112414 A1 | 5/2007 | Parker et al. |
| 2007/0112416 A1 | 5/2007 | Shanley et al. |
| 2007/0112417 A1 | 5/2007 | Shanley et al. |
| 2007/0112421 A1 | 5/2007 | O'Brien |
| 2007/0151638 A1 | 7/2007 | Burgermeister et al. |
| 2007/0173787 A1 | 7/2007 | Huang et al. |
| 2007/0173923 A1 | 7/2007 | Savage et al. |
| 2007/0191816 A1 | 8/2007 | Behan et al. |
| 2007/0202147 A1 | 8/2007 | Kleiner et al. |
| 2007/0219628 A1 | 9/2007 | Shanley et al. |
| 2007/0224116 A1 | 9/2007 | Chandrasekaran et al. |
| 2007/0224235 A1 | 9/2007 | Tenney et al. |
| 2007/0255393 A1 | 11/2007 | Flanagan |
| 2007/0259116 A1 | 11/2007 | Nolan et al. |
| 2008/0051881 A1 | 2/2008 | Feng et al. |
| 2008/0057101 A1 | 3/2008 | Roorda |
| 2008/0071344 A1 | 3/2008 | Silberg et al. |
| 2008/0071349 A1 | 3/2008 | Atanasoska et al. |
| 2008/0071351 A1 | 3/2008 | Flanagan et al. |
| 2008/0071355 A1 | 3/2008 | Weber et al. |
| 2008/0082162 A1 | 4/2008 | Boismier et al. |
| 2008/0086113 A1 | 4/2008 | Tenney et al. |
| 2008/0097349 A1 | 4/2008 | Dillinger |
| 2008/0097569 A1 | 4/2008 | O'Connor et al. |
| 2008/0147177 A1 | 6/2008 | Scheuermann et al. |
| 2008/0188836 A1 | 8/2008 | Weber et al. |
| 2008/0208325 A1 | 8/2008 | Helmus et al. |
| 2008/0275543 A1 | 11/2008 | Lenz et al. |
| 2008/0294236 A1 | 11/2008 | Anand et al. |

FOREIGN PATENT DOCUMENTS

| | | |
|---|---|---|
| DE | 3516411 | 11/1986 |
| DE | 3608158 | 9/1987 |
| DE | 9014845 | 2/1991 |
| DE | 29701758 | 3/1997 |
| DE | 29701883 | 5/1997 |
| DE | 19855421 | 5/2000 |
| DE | 19921788 | 11/2000 |
| DE | 10064596 | 6/2002 |
| DE | 10150995 | 4/2003 |
| DE | 10200387 | 8/2003 |
| DE | 102005010100 | 9/2006 |
| DE | 10107339 | 2/2009 |
| EP | 0479730 | 10/1991 |
| EP | 0565796 | 10/1993 |
| EP | 0751752 | 1/1997 |
| EP | 0783873 | 7/1997 |
| EP | 0804907 | 11/1997 |
| EP | 0815806 A2 | 1/1998 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0950386 | 10/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 1132058 | 9/2001 |
| EP | 0808140 | 12/2001 |
| EP | 1159934 | 12/2001 |
| EP | 0884028 | 2/2002 |
| EP | 1190685 | 3/2002 |
| EP | 0897700 | 7/2002 |
| EP | 1235560 | 9/2002 |
| EP | 1236447 | 9/2002 |
| EP | 1254673 | 11/2002 |
| EP | 1277449 | 1/2003 |
| EP | 1308179 | 5/2003 |
| EP | 1310242 | 5/2003 |

| | | | | | |
|---|---|---|---|---|---|
| EP | 1348402 | 10/2003 | WO | 00/44309 | 8/2000 |
| EP | 1362603 | 11/2003 | WO | 00/47134 | 8/2000 |
| EP | 0684022 | 2/2004 | WO | 00/48531 | 8/2000 |
| EP | 1402849 | 3/2004 | WO | 00/49951 | 8/2000 |
| EP | 1449546 | 8/2004 | WO | 00/51523 | 9/2000 |
| EP | 1319416 | 11/2004 | WO | 00/57813 | 10/2000 |
| EP | 1011529 | 1/2005 | WO | 00/67673 | 11/2000 |
| EP | 1157674 | 7/2005 | WO | 00/71054 | 11/2000 |
| EP | 1570808 | 9/2005 | WO | 00/71055 | 11/2000 |
| EP | 1031330 | 11/2005 | WO | 00/74595 | 12/2000 |
| EP | 1604697 | 12/2005 | WO | 0072907 | 12/2000 |
| EP | 1070513 | 6/2006 | WO | 01/17577 | 3/2001 |
| EP | 1685861 A2 | 8/2006 | WO | 01/21095 | 3/2001 |
| EP | 1359865 | 11/2006 | WO | 01/21109 | 3/2001 |
| EP | 1779816 | 5/2007 | WO | 01/21244 | 3/2001 |
| EP | 1886703 | 2/2008 | WO | 01/26584 | 4/2001 |
| EP | 1891988 | 2/2008 | WO | 01/35715 | 5/2001 |
| EP | 1891995 | 2/2008 | WO | 01/35863 | 5/2001 |
| EP | 1935508 | 6/2008 | WO | 0135928 | 5/2001 |
| EP | 1952789 | 8/2008 | WO | 01/39697 | 6/2001 |
| FR | 2678508 | 1/1993 | WO | 01/39699 | 6/2001 |
| FR | 2740346 | 10/1995 | WO | 01/41677 | 6/2001 |
| FR | 2756173 | 11/1996 | WO | 01/43665 | 6/2001 |
| GB | 2337002 | 5/1998 | WO | 01/43809 | 6/2001 |
| GB | 012198.7 | 9/2001 | WO | 01/45785 | 6/2001 |
| GB | 2397233 | 7/2004 | WO | 01/49342 | 7/2001 |
| JP | 2005160600 | 6/2005 | WO | 01/54621 | 8/2001 |
| JP | 2006175017 | 7/2006 | WO | 01/54622 | 8/2001 |
| WO | 88/06026 | 8/1988 | WO | 01/58385 | 8/2001 |
| WO | 9306792 | 4/1993 | WO | 01/60284 | 8/2001 |
| WO | 94/23787 | 10/1994 | WO | 01/66036 | 9/2001 |
| WO | 95/21592 | 8/1995 | WO | 01/70294 | 9/2001 |
| WO | 96/29955 | 10/1996 | WO | 01/70299 | 9/2001 |
| WO | 96/34580 | 11/1996 | WO | 01/74273 | 10/2001 |
| WO | 96/41592 | 12/1996 | WO | 01/89409 | 11/2001 |
| WO | 97/07752 | 3/1997 | WO | 01/91918 | 12/2001 |
| WO | 97/15346 | 5/1997 | WO | 01/93781 | 12/2001 |
| WO | 97/16217 | 5/1997 | WO | 02/00138 | 1/2002 |
| WO | 97/26936 | 7/1997 | WO | 0247581 | 6/2002 |
| WO | 97/41803 | 11/1997 | WO | 02/053066 | 7/2002 |
| WO | 97/45073 | 12/1997 | WO | 02060506 | 8/2002 |
| WO | 97/46174 | 12/1997 | WO | 02/068012 | 9/2002 |
| WO | 98/19628 | 5/1998 | WO | 03/007842 | 1/2003 |
| WO | 98/23228 | 6/1998 | WO | 03/055414 | 7/2003 |
| WO | 98/36709 | 8/1998 | WO | 03055414 | 7/2003 |
| WO | 98/36784 | 8/1998 | WO | 03/063924 | 8/2003 |
| WO | 98/37833 | 9/1998 | WO | 2004006983 | 1/2004 |
| WO | 9838946 | 9/1998 | WO | 2004/026174 | 4/2004 |
| WO | 98/47447 | 10/1998 | WO | 2004/026180 | 4/2004 |
| WO | 98/48879 | 11/1998 | WO | 2004026281 | 4/2004 |
| WO | 99/03426 | 1/1999 | WO | 2004043298 | 5/2004 |
| WO | 99/04726 | 2/1999 | WO | 2004043292 | 7/2004 |
| WO | 99/15103 | 4/1999 | WO | 2004058100 | 7/2004 |
| WO | 99/15108 | 4/1999 | WO | 2004064911 | 8/2004 |
| WO | 99/15109 | 4/1999 | WO | 2005/009295 | 2/2005 |
| WO | 99/23977 | 5/1999 | WO | 2005/014077 | 2/2005 |
| WO | 99/24104 | 5/1999 | WO | 2005/041810 | 5/2005 |
| WO | 99/29262 | 6/1999 | WO | 2005051450 | 6/2005 |
| WO | 99/34749 | 7/1999 | WO | 2005077305 | 8/2005 |
| WO | 99/36002 | 7/1999 | WO | 2005082277 | 9/2005 |
| WO | 99/36015 | 7/1999 | WO | 2005089673 | 9/2005 |
| WO | 99/44539 | 9/1999 | WO | 2005110285 | 11/2005 |
| WO | 99/56661 | 11/1999 | WO | 2005/122959 | 12/2005 |
| WO | 99/65419 | 12/1999 | WO | 2006/028925 | 3/2006 |
| WO | 00/07523 | 2/2000 | WO | 2006029708 A1 | 3/2006 |
| WO | 00/10489 | 3/2000 | WO | 2006/074476 | 7/2006 |
| WO | 00/16719 | 3/2000 | WO | 2006098889 A2 | 9/2006 |
| WO | 00/27307 | 5/2000 | WO | 2006099450 | 9/2006 |
| WO | 00/27463 | 5/2000 | WO | 2006/127127 | 11/2006 |
| WO | 00/28922 | 5/2000 | WO | 2007031968 | 3/2007 |
| WO | 01/45594 | 6/2000 | WO | 2007031972 | 3/2007 |
| WO | 0037138 | 6/2000 | WO | 2007059253 | 5/2007 |
| WO | 00/44307 | 8/2000 | WO | 2007118139 | 10/2007 |

| | | |
|---|---|---|
| WO | 2008016528 | 2/2008 |
| WO | 2008073208 | 6/2008 |

OTHER PUBLICATIONS

Katoh, M.D., Osamu, "New Double Wire Technique to Stent Ostial Lesions," Catheterization and Cardiovascular Diagnosis, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).

Yamashita, M.D., PhD., Takehiro, "Birfurcation Lesions: Two Stents Versus One Stent—Immediate and Follow-up Results," Journal of the American College of Cardiology, vol. 35:5, pp. 1145-1151 (Apr. 2000).

Satler, M.D., Lowell F., "Bifurcation Disease: To Treat or Not to Treat," Catheterization and Cardiovascular Interventions, vol. 50, pp. 411-412 (2000).

U.S. Appl. No. 60/844,011, filed Sep. 12, 2006; Inventor: Broome et al.

U.S. Appl. No. 09/663,111, filed Sep. 15, 2000; Inventor: Davidson et al.

U.S. Appl. No. 09/614,472, filed Jul. 11, 2000; Inventor: Davidson et al.

U.S. Appl. No. 09/325,996, filed Jun. 4, 1999; Inventor: Vardi et al.

Chevalier, M.D., Bernard, "Placement of Coronary Stents in Bifurcation Lesions by the "Culotte" Technique," The American Journal of Cardiology, vol. 82, pp. 943-949 (Oct. 15, 1998).

Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).

Caputo, Ronald P., "Stent Jail: A Minimum-Security Prison," The American Journal of Cardiology, vol. 77, pp. 1226-1230 (Jun. 1, 1996).

Colombo, M.D., Antonio, ""Kissing" Stent for Bifurcational Coronary Lesions," Catheterization and Cardiovascular Diagnosis, vol. 30, pp. 327-330 (Dec. 1993).

* cited by examiner

BIFURCATED STENT WITH DRUG WELLS FOR SPECIFIC OSTIAL, CARINA, AND SIDE BRANCH TREATMENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Thus stenoses at bifurcations can be classified based on the location of the stenoses relative to the bifurcation, as is done in the ICPS Plaque Distribution Classification and the Duke Plaque Distribution Classification. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent that elutes different volumes of at least one therapeutic agent from different regions of the stent. In at least one embodiment, a region of the stent elutes a therapeutic agent with a different concentration than a therapeutic agent eluted from at least one other region of the stent. In at least one embodiment, a region of the stent elutes a therapeutic agent at a different rate than at least one other region of the stent.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
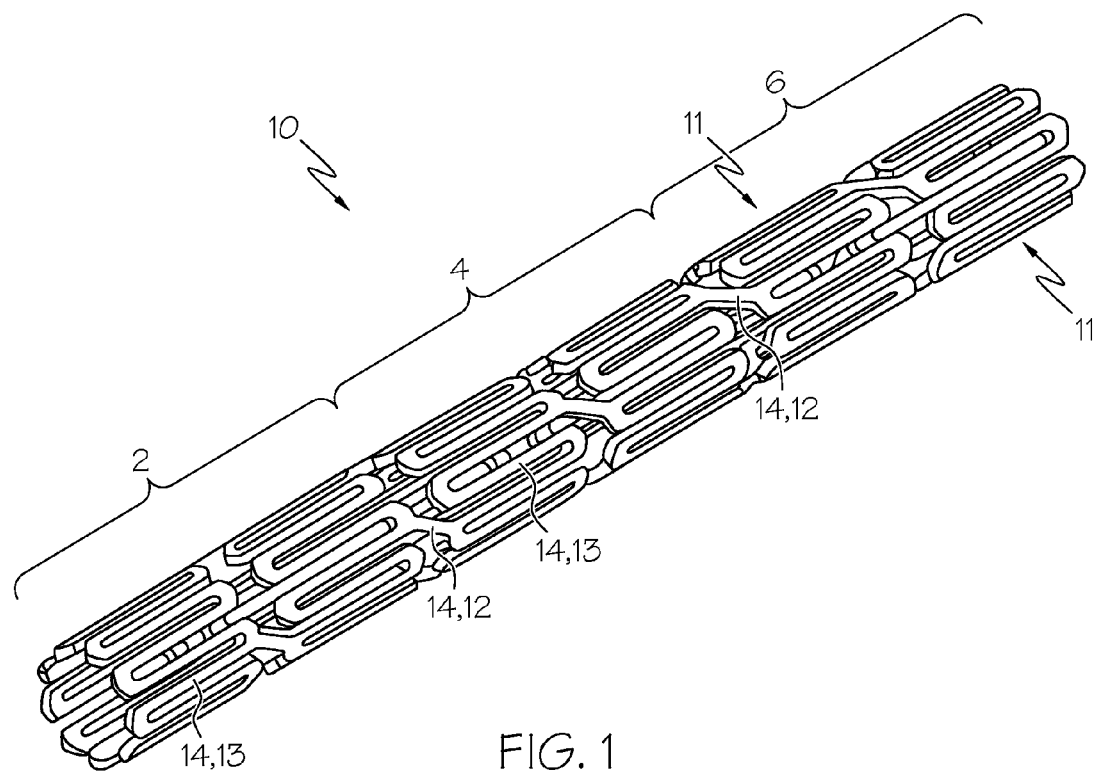
FIG. 1 is a perspective view of a stent comprising a plurality of members.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 3:
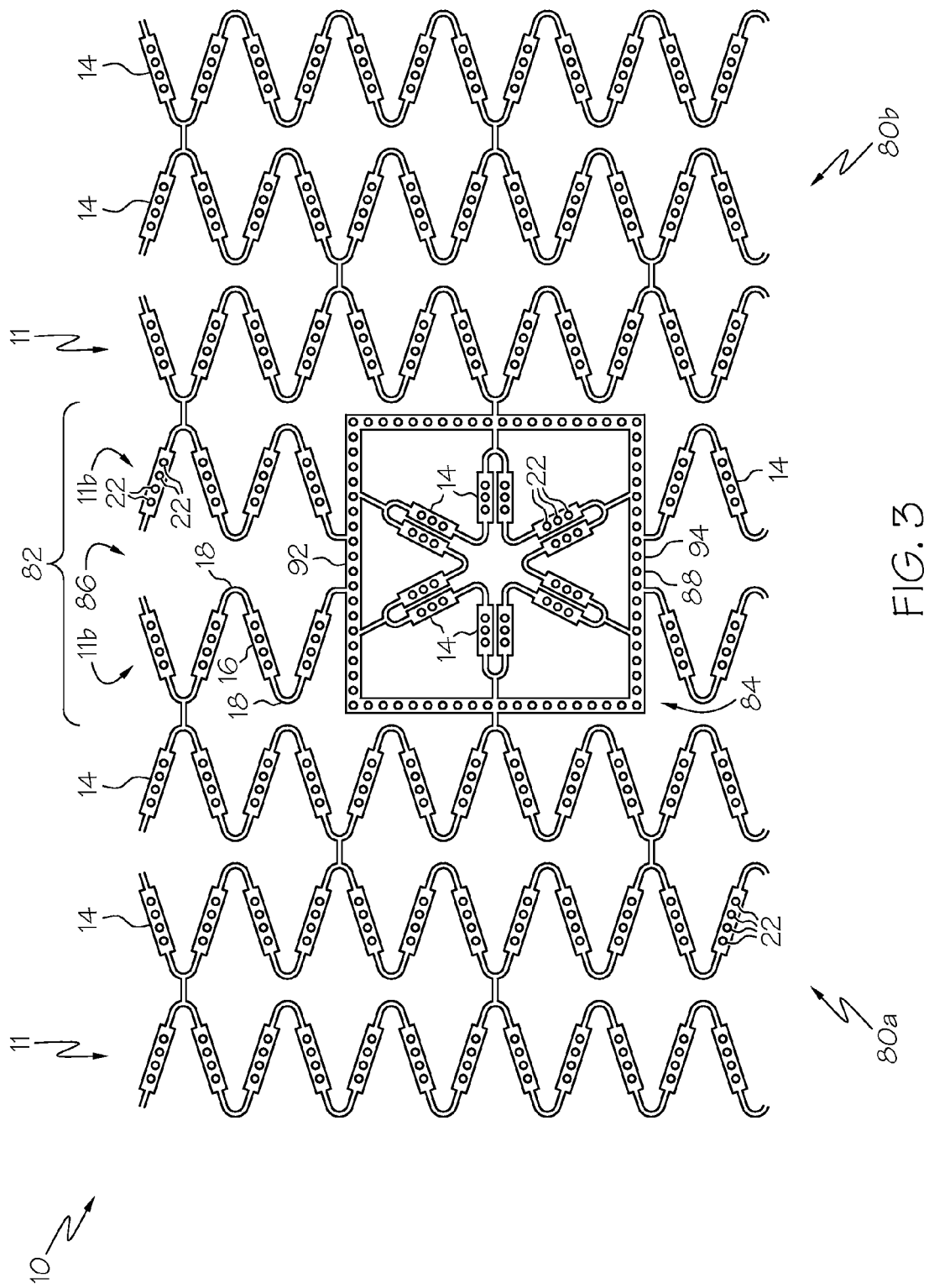
FIG. 3 is a flat view of a bifurcated stent comprising a plurality of members and coating retainers.

FIGS. 1 and 3 depict a stent 10 comprising a plurality of members 14 that form circumferential rings 11 that extend about the circumference of the stent 10. The stent 10 illustrated in FIG. 1 is an example of a configuration for a non-bifurcated stent 10 and the stent 10 in FIG. 3 is an example of a configuration for a bifurcated stent 10. The stent 10 configurations in FIGS. 1 and 3 are presented as non-limiting examples of stent 10 configurations that can be used to deliver therapeutic regimens, it is within the scope of the invention for any stent 10 configuration to be used.

Members 14, as used in this application, include both struts 13 and connectors 12. In at least one embodiment, the struts 13 have substantially the same width and substantially the same thickness along the length of the strut 13. In some embodiments, the struts 13 have substantially the same thickness along the length of the strut 13. In other embodiments, the struts 13 have substantially the same width along the length of the strut 13. In at least one embodiment, the connectors 12 have substantially the same width and substantially the same thickness along the length of the connector 12. In some embodiments, the connectors 12 have substantially the same width along the length of the connector 12. In other embodiments, the connectors 12 have substantially the same thickness along the length of the connector 12.

The width of the member 14 is the distance between one circumferential side of the member 14 to the other circumferential side of the member 14. The thickness of the member 14 is the distance from the luminal surface of the member 14 to the abluminal surface of the member 14. The length of the member 14 that is straight is the distance from the proximal end of the member 14 to the distal end of the member 14. The length of the member 14 that is not straight is the distance of the pathway from the proximal end of the member 14 to the distal end of the member 14

Figure 2:
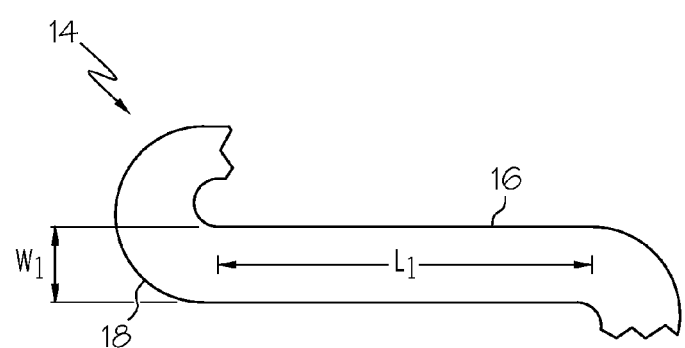
FIG. 2 is an enlarged view of one of the plurality of members of FIG. 1.

Some of the members 14 have at least one straight section 16 and at least one turn 18, as shown for example, in FIG. 2. The straight section 16 of the member 14 may be the same width as the at least one turn 18, as shown for example in FIG. 1, or may be wider than the at least one turn 18, as shown for example in FIG. 3. Each member 14 has four sides from which therapeutic agents can be eluted: the abluminal side (side of member 14 adjacent to the lumen wall), the luminal side (side of member 14 adjacent to the lumen) and the other two sides of the member 14 which are at an oblique angle to the luminal and abluminal sides of the member 14. As used in this application, an oblique angle is any angle between 0 and 180 degrees and includes 90 degrees. Each member 14 has a length ($L_1$), a width ($W_1$) and a depth (not shown in FIG. 2).

Stents 10 have different regions and/or subregions. As a non-limiting example, the stent 10 in FIG. 1 can be divided into a proximal region 2, a middle region 4 and a distal region 6, where each region has two circumferential rings 11 of members 14. One of ordinary skill in the art will recognize that there are numerous ways in which the stent 10 of FIG. 1 can be designed to have different regions and/or subregions that have different sizes and positions along the longitudinal length of the stent 10. Thus, it is within the scope of the invention for a stent 10 to have one, two, three, four, five, six, seven, eight, nine, ten, eleven, twelve, thirteen, fourteen, fifteen, sixteen, seventeen, eighteen, nineteen, twenty or more regions.

Similarly, a bifurcated stent 10 has several regions. These regions include for example, a proximal main branch region 80a, a middle region 82 and a distal main branch region 80b, as illustrated in FIG. 3. The proximal main branch region 80a and the distal main branch region 80b each comprise at least one circumferential ring 11. The middle region 82 comprises a side branch 84 and a contralateral region 86. The circumferential rings 11b of the contralateral region 86 extend from a first side 92 of the side branch 84 about the circumference of the stent 10 to the second side 94 of the side branch 84. The side branch 84 has at least one side branch member 14 and a perimeter member 88 that defines the opening for the expandable side branch 84. The members 14 of the side branch 84 are a non-limiting example of a subregion of the side branch 84 region of the stent 10. The perimeter member 88 can have any shape, including, but not limited to, an oval, circular or rectangular shape. The perimeter member 88 can be a separate and distinct member 14 from the other members 14 of the stent 10 or the perimeter member 88 can be formed by some of the members 14 of the stent 10.

In at least one embodiment, the invention is directed to a stent 10 that elutes multiple therapeutic regimens from different regions and/or subregions of the stent 10. To deliver multiple therapeutic regimens, the stent 10 has any mechanism designed to deliver at least one therapeutic agent, including prior art means for delivering therapeutic agents, coating retainers 22, or any combination thereof. Different types of coating retainers 22 are discussed in greater detail in Stent Design Allowing Extended Release of Drug and/or Enhanced Adhesion of Polymer to OD Surface, application Ser. No. 11/857,736, hereby incorporated by reference in its entirety. Note that coating retainers 22 can have different configurations but elute the same volume of therapeutic agent or the same configuration can be in different sizes that elute different volumes of therapeutic agent. For simplicity, the term coating retainer 22, as used in this application, refers to any mechanism designed to deliver at least one therapeutic agent that is either formed (partially or completely) within the body of the members 14 of the stent 10 or engaged to the body of the members 14 of the stent 10. The coating retainers 22 are positioned on at least one side of the members 14 comprising the different regions and/or subregions of the stent 10.

Pressure differentials are one reason to configure a stent 10 to deliver multiple therapeutic regimens from different regions since differences in pressure could alter the reactivity of the therapeutic agent. Thus, it can be advantageous to appropriately vary the relative types, concentrations, volumes or elution rate of a therapeutic agent on different regions of the stent 10. For example, with a bifurcated stent 10 it can be advantageous to have different types, concentrations, volumes or elution rate in the main branch region 80 as compared to the side branch region 84, as discussed in greater detail below. Another reason to use a stent 10 that can deliver multiple therapeutic regimens is to target the therapies to the regions of the stent 10 that are in contact with the sites of the body lumen that requires the therapies. For example, the stent 10 can be designed so that only the region of the stent 10 in contact with a stenosis would deliver/elute a therapeutic agent to treat the stenosis.

In at least one embodiment, at least one region of the stent 10 delivers a different therapeutic regimen than at least one other region of the stent 10. Thus a single stent 10 delivers at least two therapeutic regimens. In at least one embodiment, each region of the stent 10 delivers a different therapeutic regimen. Different therapeutic regimens include, but are not limited to, different therapeutic agents, different concentrations of therapeutic agent, different local concentrations of therapeutic agent, different volumes of therapeutic agent, different elution rates of therapeutic agent/different durations of release of therapeutic agent, different release kinetics of therapeutic agent and any combination thereof. The different therapeutic regimens can be used singly or in combination with one or more of the different regions of the stent 10.

Different ways to affect the elution rate/duration of release include, but are not limited to, including a non-active material in some of the coating retainers 22, changing the formulation of therapeutic agent within some of the coating retainers 22, creating a barrier layer over the therapeutic agent deposited in some of the coating retainers 22 and any combination thereof. In some embodiments, the non-active material in the coating retainer 22 increases the surface area to volume ratio for the therapeutic agent, thereby affecting the duration of release of the therapeutic agent. Changing the formulation of therapeutic agent includes, but is not limited to, changing the ratios of therapeutic agents, changing the types of therapeutic agents, changing the loading of the therapeutic agent. In at least one embodiment, a barrier layer over the therapeutic agent slows the release of therapeutic agent, thereby extending the therapeutic agent's duration of release. The use of barrier layers is discussed in commonly assigned application Ser. No. 11/857,736, entitled Stent Design Allowing Extended Release of Drug and/or Enhanced Adhesion of Polymer to OD Surface.

Different release kinetics include rate of short term release, rate of long term release, local concentration of therapeutic agent and duration of effect. The rate of release can be modulated by drug/carrier ratios, surface area, total volume of therapeutic agent and macroscopic distribution of therapeutic agent in the vessel.

The different therapeutic regimens are discussed in greater detail below in reference to a stent 10 that can be used at a bifurcation, as shown in FIG. 3. However, as discussed above, any stent 10 configuration can be configured to deliver at least two therapeutic regimens. Furthermore, the embodiments shown in FIGS. 3-7 illustrate the invention as applied to one side of the stent 10, e.g. abluminal. As discussed above, it is within the scope of the invention for both sides of the stent 10 to deliver multiple therapeutic regimens. Note that for simplicity, the stents 10 in FIGS. 3-7 all have the same type of coating retainer 22 but it is within the scope of the invention for different regions and or subregions of the stent 10 to have different types of coating retainers 22, as discussed above.

In at least one embodiment, a stent 10 delivers different volumes of therapeutic agent from different regions of the stent 10. Different volumes of therapeutic agent can be delivered by different regions of the stent 10 due to different volumes of therapeutic agent deposited in/on coating retainers 22 of the different regions of the stent 10, different types of coating retainers 22 in each region of the stent 10, different sizes of coating retainers 22, different numbers of coating retainers 22 in each region of the stent 10, and any combination thereof.

In at least one embodiment, different volumes of therapeutic agent are deposited in/on the coating retainers 22 of the different regions of the stent 10. In one embodiment, all the coating retainers 22 on the stent 10 are the same size/volume and each region of the stent 10 has the same number of coating retainers 22 and different regions of the stent 10 have different volumes of therapeutic agent applied thereto. In this embodiment, all the coating retainers 22 are sized to hold the greatest volume of therapeutic agent deposited onto the stent 10 and some coating retainers 22 have the greatest volumes deposited therein/thereon while some coating retainers 22 have smaller volumes of therapeutic agent deposited therein/on so that they are "under-filled" with therapeutic agent. In this embodiment, the manufacture of the stent 10 is simplified since only one type and size of coating retainer 22 is required. Note that this stent 10 embodiment can also elute the same volume of therapeutic agent from the different regions of the stent 10, for example, when the same volume of therapeutic agent is applied to the entire stent 10.

In at least one embodiment, differentially sized coating retainers 22 are utilized on different regions of the stent 10. As discussed above, the volume/size of a coating retainer 22 depends upon the length, width, and depth of the coating retainer 22 and variation of at least one of the length, width and depth affects the volume of therapeutic agent that can be deposited on/in the coating retainer 22, and consequently the volume of, and/or local concentration of, therapeutic agent eluted from the coating retainer 22. In at least one embodiment, the coating retainer 22 is a hole and the diameter of the hole affects the local concentration of therapeutic agent. Thus, if the coating retainer 22 is in the form of a hole, for example, increasing the diameter of the coating retainer 22 increases the local concentration of therapeutic agent and decreasing the diameter of the coating retainer 22 decreases the local concentration of therapeutic agent. In one embodiment, the local concentration of therapeutic agent is affected at a micrometer-level scale.

To ensure that different volumes of therapeutic agent are eluted from the different regions of the stent 10, the volume of therapeutic agent deposited onto a particular region of the stent 10 should be at least equal to the total volume of all the coating retainers 22 on that region so that each coating retainer 22 contains the maximum amount of therapeutic agent. Note that, as discussed in greater detail in Stent Design Allowing Extended Release of Drug and/or Enhanced Adhesion of Polymer to OD Surface, application Ser. No. 11/857, 736, the volume of the therapeutic agent determines the length of time that the therapeutic agent elutes from the stent 10, i.e. the duration of release. Thus, coating retainers 22 with a greater volume of therapeutic agent deposited thereon/therein will elute the therapeutic agent for a longer time than a coating retainer 22 with a smaller volume of therapeutic agent deposited thereon/therein.

In at least one embodiment, at least one region of the stent 10 has a different number of coating retainers 22 than another region of the stent 10. A number of factors affect the number of coating retainers 22 in a region of the stent 10, for example, but not limited to, the density of coating retainers 22 in a region of the stent 10, the number of members 14 forming the region of the stent 10, the number of coating retainers 22 on each member 14 of a region of the stent 10, and any combination thereof.

Figure 4:
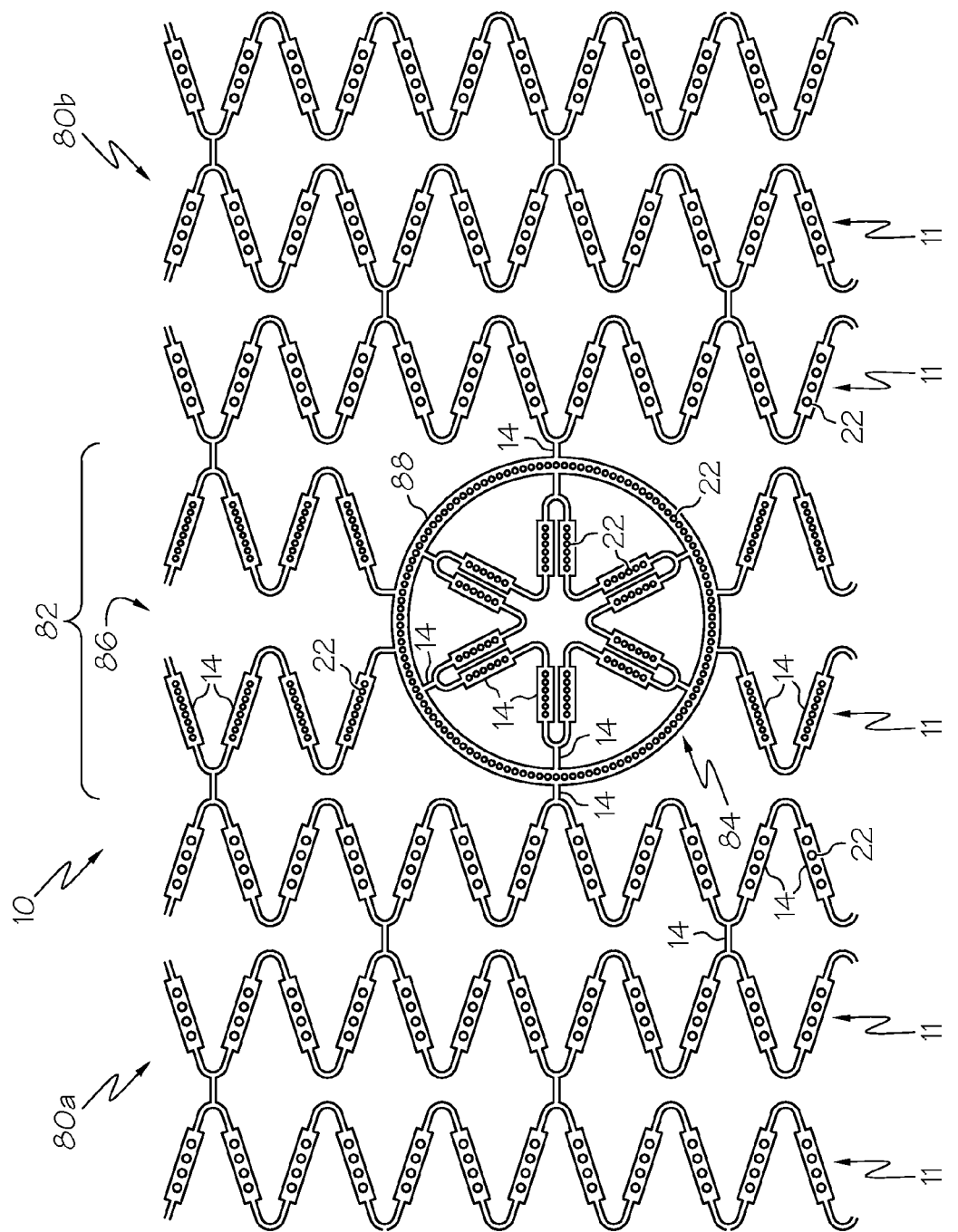
FIG. 4 is a flat view of a bifurcated stent with regions that elute different volumes of therapeutic agent.

In at least one embodiment, at least one region of the stent 10 has a different density of coating retainers 22. The density of coating retainers 22 is determined by the number of coating retainers 22 per unit of area. In at least one embodiment, the density of the coating retainers 22 affects the local concentration of therapeutic agent. Thus, the local concentration of therapeutic agent is reduced when the spacing between coating retainers 22 is increased, i.e. the density of coating retainers 22 is low, and the local concentration of therapeutic agent is increased when the spacing between coating retainers 22 is decreased, i.e. the density of coating retainers 22 is high. In on embodiment, the local concentration of therapeutic agent is affected on a millimeter-level scale. In FIG. 4, for example, the members 14 of the contralateral region 86 have a higher density of coating retainers 22 than the members 14 of the proximal main branch region 80a. In this embodiment, if two regions of the stent 10 have the same number of members 14, but the members 14 have different densities of coating retainers 22, the two regions of the stent 10 will have different numbers of coating retainers 22.

In at least one embodiment, different regions of the stent 10 have different densities of coating retainers 22 and the coating retainers 22 have different sizes. This can occur, for example, if the depth (thickness) of the members 14 with the higher density of coating retainers 22 is not sufficiently large to adjust the size of the coating retainer 22 so that it is the same as the size of the coating retainers 22 with a lower density without affecting the integrity of the member 14.

In at least one embodiment, different regions of the stent 10 have different densities of coating retainers 22 and the coating retainers 22 have the same size. This can occur, for example, if the depth of the members 14 is sufficiently large so that the higher density coating retainers 22 positioned within the member 14 have a greater depth than the lower density coating retainers 22 positioned within the member 14. In this embodiment, the greater depth of the higher density coating retainers 22 causes the higher density coating retainers 22 to elute therapeutic agent for a longer period of time than the lower density coating retainers 22 even though the same total amount of therapeutic agent would be eluted by both the higher density and the lower density coating retainers 22.

In at least one embodiment, not illustrated, a different number of members 14 comprise at least one region of the stent 10, where each member 14 has the same number of coating retainers 22. Note that the density of the coating retainers 22 in the regions of the stent 10 can be the same or different so long as each member 14 of the stent 10 has the same number of coating retainers 22. In one embodiment, different regions of the stent 10 have different numbers of circumferential rings 11 where each circumferential ring 11 comprises the same number of members 14. Thus, if the proximal main branch region 80a has four circumferential rings 11 each comprising ten members 14 and the distal main branch region 80b has three circumferential rings 11 each comprising ten members 14, the proximal main branch region 80a has a greater number of coating retainers 22 than the distal main branch region 80b.

In one embodiment, different regions of the stent 10 have the same number of circumferential rings 11 but one region of the stent 10 has at least one circumferential ring 11 with a different number of members 14. Thus, the proximal main branch region 80a will have a greater number of coating retainers 22 where both the proximal main branch region 80a and the distal main branch region 80b have three circumferential rings 11 but the one of the circumferential rings 11 of the proximal main branch region 80a has a greater number of members 14 than the number of members 14 comprising the other circumferential rings 11.

In one embodiment, at least one region of the stent 10 has a different number of coating retainers 22 because it has a different number of members 14 and a different density of coating retainers 22 than another region of the stent 10. For example, a region of the stent 10 with a greater number of members 14 and a higher density of coating retainers 22 will have more coating retainers 22 than another region of the stent 10 with a fewer number of members 14 and a lower density of coating retainers 22. Note that a first region with a higher density of coating retainers 22 and fewer members 14 than a second region can be designed to have the same number of coating retainers 22 as the second region.

In at least one embodiment, different regions of the stent 10 have different numbers of coating retainers 22 on each member 14 of the region. In one embodiment, the density of the coating retainers 22 is the same in different regions of the stent 10 but the total number of coating retainers 22 varies between regions of the stent 10. In one embodiment, the different regions of the stent 10 have members 14 with different lengths. In one embodiment, different members 14 of a region of the stent 10 have different lengths where the members 14 have different numbers of coating retainers 22 but the same density of coating retainers 22, as discussed below in reference to FIG. 7.

FIGS. 3-7 illustrate many of the design embodiments discussed above. As these non-limiting examples described below illustrate, there are numerous configurations and designs that exemplify embodiments of this invention. The stent 10 in FIG. 3 has a side branch 84 where each of the plurality of members 14 has three coating retainers 22 and a square shaped perimeter member 88 with seventy-six (76) coating retainers 22. The contralateral region 86 has a total of forty-eight (48) coating retainers 22. Note that the length of the members 14 in the side branch 84 is less than the length of the members 14 of the contralateral region 86 but the density of the coating retainers 22 is the same for both regions. The proximal main branch region 80a and the distal main branch region 80b each have a total of one hundred forty-four (144) coating retainers 22. Note that although the members 14 of the proximal main branch region 80a, the contralateral region 86 and the distal main branch region 80b each have four coating retainers 22, if all the coating retainers 22 are the same size, the contralateral region 86 elutes a smaller total volume of therapeutic agent than either the proximal main branch region 80a or the distal main branch region 80b. Also note that if the coating retainers 22 are the same size and have the same amount of therapeutic agent deposited therein/thereon, each of the proximal main branch region 80, the distal main branch region 80b, the contralateral region 86 and the members 14 of the side branch 84 will elute the therapeutic agent for the same amount of time.

In FIG. 4, each member 14 of the side branch 84 has six coating retainers 22, each member 14 of the contralateral region 86 has eight coating retainers 22 and each member 14 of the proximal and distal main branch regions 80a,b has four coating retainers 22. The perimeter member 88 in this embodiment has one hundred and twenty (120) coating retainers 22. In this embodiment, the members 14 of the proximal main branch region 80a and the members 14 of the contralateral region 82 have the same length but the density of the coating retainers 22 of the proximal section 80 is half the density of the coating retainers 22 of the contralateral section 82. The proximal and distal main branch regions 80a,b each have a total of one hundred forty-four (144) coating retainers 22 while the contralateral region 86 has a total of one hundred ninety-two (192) coating retainers 22. Thus, in this embodiment, if all the coating retainers 22 are the same size, the contralateral region 86 elutes a greater total volume of therapeutic agent than either the proximal main branch region 80a or the distal main branch region 80b. If the coating retainers 22 of the contralateral region 86 are smaller than the coating retainers 22 of the proximal main branch region 80a and the distal main branch region 80b, the proximal and distal main branch regions 80a,b will elute therapeutic agent for a longer period of time than the contralateral region 86.

Figure 5:
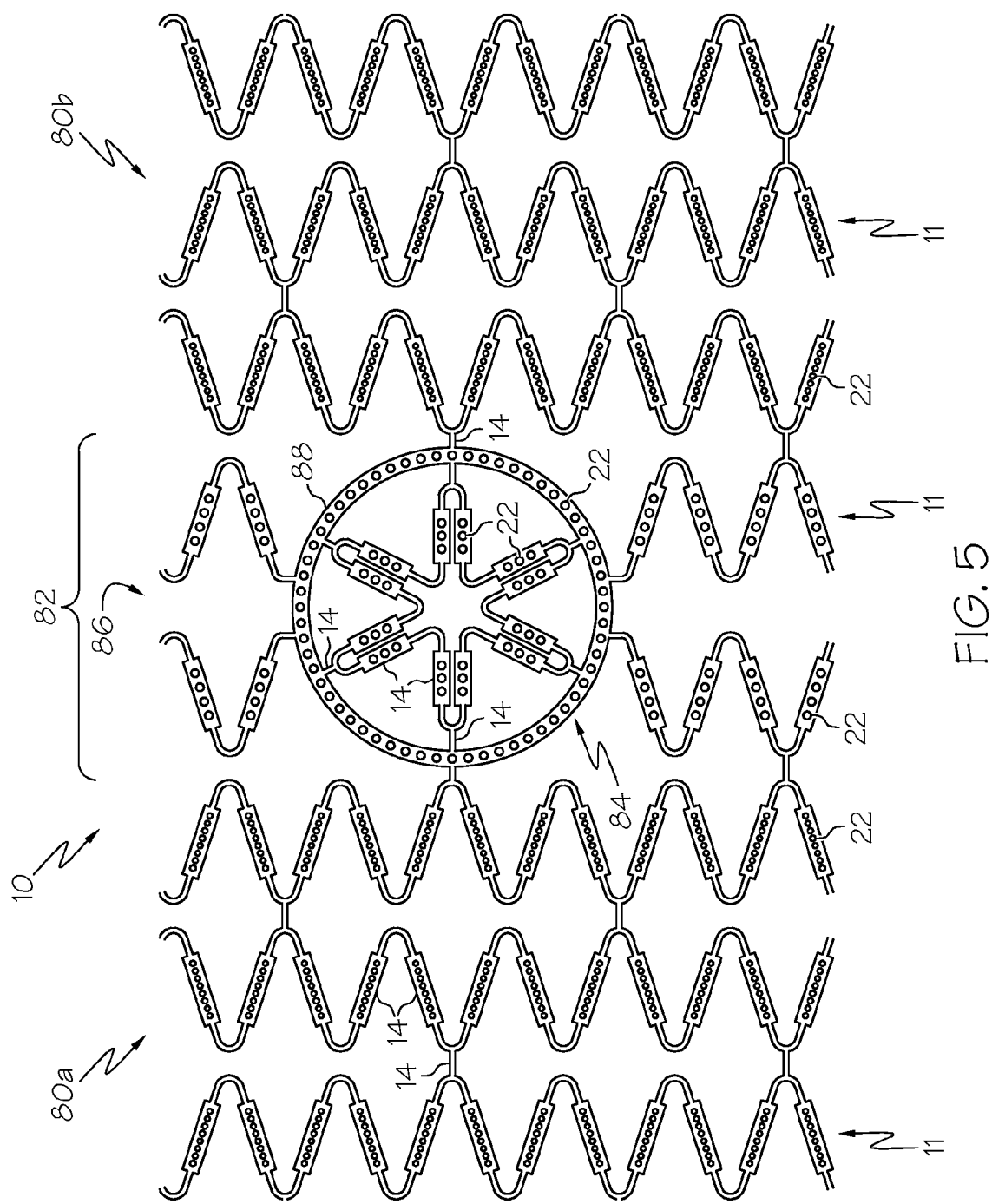
FIG. 5 is a flat view of another bifurcated stent with regions that elute different volumes of therapeutic agent.

In FIG. 5, each member 14 of the side branch 84 has three coating retainers 22, each member 14 of the contralateral region 86 has four coating retainers 22, each member 14 of the proximal and distal main branch regions 80a,b have eight coating retainers 22, and the perimeter member 88 has sixty (60) coating retainers 22. In this embodiment, the proximal and distal main branch regions 80a,b have a higher density of coating retainers 22 than the contralateral region 86 and the side branch region 84, and the contralateral region 86 has a greater density of coating retainers 22 than the side branch region 84. Thus, the stent 10 comprises three regions that have different densities of coating retainers 22. The proximal and distal main branch regions 80a,b each have a total of two hundred eighty-eight (288) coating retainers 22 while the contralateral region 86 has a total of ninety-six (96) coating retainers 22. Thus, in this embodiment, if all the coating retainers 22 are the same size, the proximal main branch region 80a and the distal main branch region 80b each elute a greater volume of therapeutic agent than the contralateral region 86, in contrast to the stent 10 in FIG. 4. If the coating retainers 22 of the contralateral region 86 are larger than the coating retainers 22 of the proximal main branch region 80a and the distal main branch region 80b, the proximal and distal main branch regions 80a,b will elute therapeutic agent for a shorter period of time than the contralateral region 86.

Figure 6:
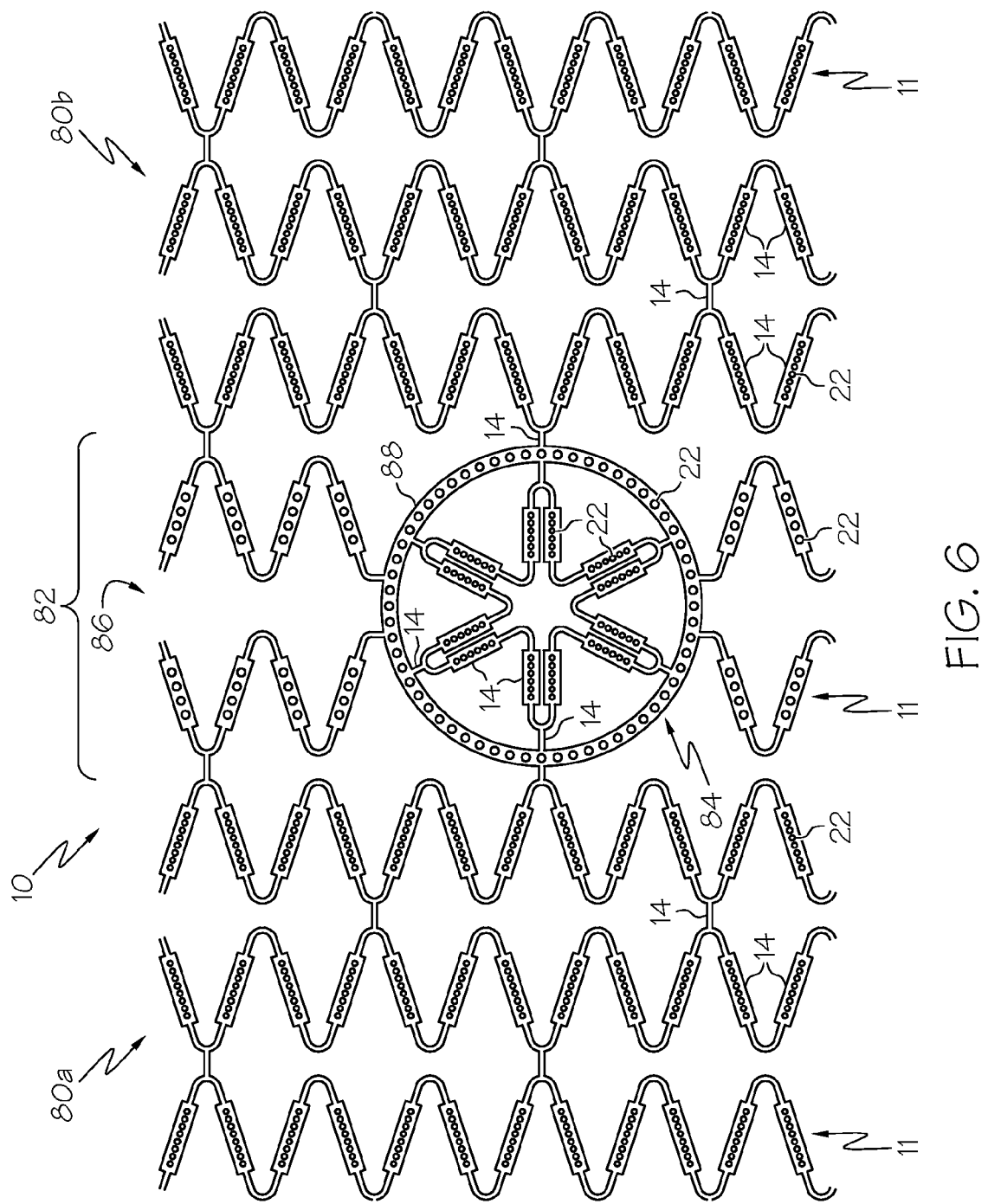
FIG. 6 is a flat view of another bifurcated stent with regions that elute different volumes of therapeutic agent.

FIG. 6 has the same configuration as FIG. 5 except that each member 14 of the side branch 84 has six coating retainers 22, instead of three coating retainers 22 as shown in FIG. 5. Since the length of the members 14 are substantially the same, the members 14 forming the side branch 84 of FIG. 6 have a greater density of coating retainers 22 than the members 14 of the side branch 84 in FIG. 5. In addition, the coating retainers 22 of the members 14 of the side branch 84 in FIG. 5 are larger than the coating retainers 22 of the members 14 of the side branch 84 in FIG. 6. Therefore, the side branch 84 of FIG. 5 will elute therapeutic agent for a longer period of time than the side branch 84 of FIG. 6.

Figure 7:
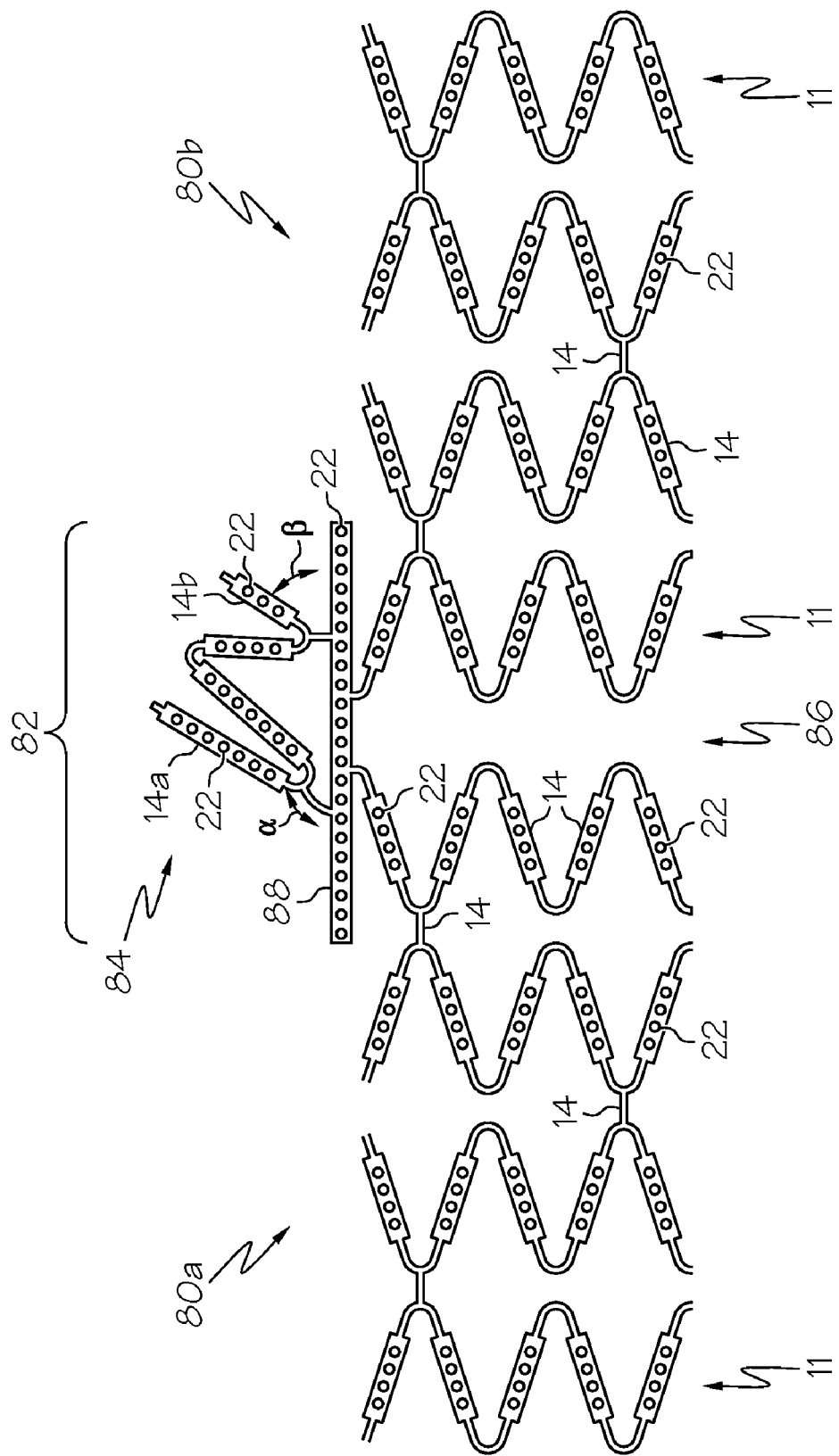
FIG. 7 is a side view of a bifurcated stent in an expanded state, with the side branch at an oblique angle to the main body of the stent.

In FIG. 7, members 14a,b of the side branch 84 each have different numbers of coating retainers 22 (seven coating retainers 22 on member 14a and three coating retainers 22 on member 14b) although each member 14a,b has the same density of coating retainers 22 due to the different lengths of the members 14a,b. In this embodiment, member 14a will elute a greater total volume of therapeutic agent than member 14b but both members 14a,b will elute the therapeutic agent for the same length of time if the coating retainers 22 are the same size.

In this embodiment, the side branch 84, which is in an expanded state, is at an oblique angle to the main branch 80 of the stent 10. Note that the distal angle (β) of the side branch 84 to the proximal main branch region 80a is more acute than the proximal angle (α) of the side branch 84 to the distal main branch region 80b. There is a correlation between the acuteness of the angle and the stress on the member(s) 14b of the side branch 84 closest to the acute angle. Because of this stress, the maximum possible number of equally sized coating retainers 22 on the member(s) 14b is less than the maximum possible number of equally sized coating retainers 22 on the member(s) 14a of the side branch 84 closest to the less acute angle (α). The stress will also affect the length, width and depth of the coating retainers 22 on a member 14 as well as the distance between coating retainers 22 on a member 14. Because the perimeter member 88 is engaged to the member(s) 14 of the side branch 84, it also experiences stress that can affect the number and size of the coating retainers 22 positioned on the perimeter member 88.

Also note that, in this embodiment, the members 14 of the side branch 84 have different lengths, with the proximal member 14a having a greater length than the distal member 14b. This design allows the members 14 of the side branch 84 to extend to a uniform distance into the side branch vessel when the side branch 84 is at an oblique angle to the main branch 80 of the stent 10. It is within the scope of the invention for the members 14 of the side branch 84 to have the same length.

The following numbered statements characterize at least one of the embodiments described above:

1. A stent, the stent having a body comprising a plurality of members, the plurality of members defining the body of the stent, the body comprising:

a first region, the first region comprising a first plurality of first coating retainers, each of the first plurality of first coating retainers having a first volume and a first volume of therapeutic agent, the first plurality of first coating retainers eluting a first total volume of a first therapeutic agent; and a second region, the second region comprising a second plurality of second coating retainers, the second plurality of second coating retainers having a second volume and a second volume of second therapeutic agent, the second plurality of second coating retainers eluting a second total volume of a second therapeutic agent;

wherein the first volume of each of the first plurality of first coating retainers is equal to the second volume each of the second plurality of second coating retainers, the first volume of first therapeutic agent is greater than the second volume of second therapeutic agent, and the first total volume of therapeutic agent is greater than the second total volume of therapeutic agent.

2. The stent of statement 1, the first therapeutic agent being different than the second therapeutic agent.

3. The stent of statement 1, each of the plurality of members having a width and a length, the width being substantially constant along the length of the member.

4. The stent of statement 1, each of the plurality of members having a thickness and a length, the thickness being substantially constant along the length of the member.

The following numbered statements characterize at least one of the embodiments described above:

1. A stent, the stent having a body comprising a plurality of members, the plurality of members defining the body of the stent, the body comprising:

a first region, the first region having a plurality of first coating retainers, the plurality of first coating retainers having a first configuration, the first therapeutic agent eluting from the plurality of first coating retainers at a first elution rate; and a second region, the second region having a plurality of second coating retainers, the plurality of second coating retainers having a second configuration, the second therapeutic agent eluting from the plurality of second coating retainers at a second elution rate;

wherein the first elution rate is greater than the second elution rate, and the first configuration of the first coating retainers is different from the second configuration of the second coating retainers.

2. The stent of statement 1, the first therapeutic agent having a first concentration, the second therapeutic agent having a second concentration, the first concentration equal to the second concentration.

3. The stent of statement 1, the first therapeutic agent having a first concentration, the second therapeutic agent having a second concentration, the first concentration greater than the second concentration.

4. The stent of statement 1, the first region eluting a first total volume of therapeutic agent, the second therapeutic agent eluting a second total volume of therapeutic agent, the first total volume equal to the total second volume.

5. The stent of statement 1, the first region eluting a first total volume of therapeutic agent, the second therapeutic agent eluting a second total volume of therapeutic agent, the first total volume greater than the second total volume.

6. The stent of statement 5, the first configuration of the first coating retainers having a first volume, the second configuration of the second coating retainers having a second volume, the first volume equal to the second volume, the members of the first region having a first density of first coating retainers, the members of the second region having a second density of second coating retainers, the first density greater than the second density.

6. The stent of statement 1, the members of the first region having a first density of first coating retainers, the members of the second region having a second density of second coating retainers, the first density greater than the second density.

7. The stent of statement 1, the plurality of first coating retainers being formed at least partially within the body of a plurality of the members comprising the first region of the stent.

8. The stent of statement 7, the plurality of second coating retainers being formed at least partially within the body of a plurality of the members comprising the second region of the stent.

9. The stent of statement 1, wherein the first region is selected from at least one member of the group consisting of the luminal side, the abluminal side, the proximal region, the distal region, the middle region, the main body of a bifurcated stent, the contralateral region, the side branch of a bifurcated stent, members forming the side branch, the perimeter member and any combination thereof.

10. The stent of statement 9, wherein the second region is selected from at least one member of the group consisting of the luminal side, the abluminal side, the proximal region, the distal region, the middle region, the main body of a bifurcated stent, the contralateral region, the side branch of a bifurcated stent, members forming the side branch, the perimeter member and any combination thereof, the second region being different than the first region.

11. The stent of statement 1, the first configuration determined by a first length, a first width and a first depth and the second configuration determined by a second length, a second width and a second depth, wherein at least one of the first length, the first width and the first depth is different from at least one of the second length, the second width and the second depth so that the first size contains the first volume of first therapeutic agent and the second size contains the second volume of second therapeutic agent.

The following numbered statements characterize at least one of the embodiments described above:

1. A stent, the stent having a body comprising a plurality of members, the plurality of members defining the body of the stent, the body comprising:
    a first region, the first region comprising a plurality of first coating retainers, the first region having a first density of first coating retainers, the first region eluting a first total volume of first therapeutic agent from the first coating retainers;
    a second region, the second region comprising a plurality of second coating retainers, the second region having a second density of second coating retainers, the second region eluting a second total volume of second therapeutic agent from the second coating retainers;
    wherein the first density of first coating retainers is greater than the second density of second coating retainers and the first total volume of first therapeutic agent is greater than the second total volume of second therapeutic agent.

2. The stent of statement 1, each of the plurality of first coating retainers having a first configuration, each of the plurality of second coating retainers having a second configuration, the first configuration different than the second configuration.

3. The stent of statement 1, each of the plurality of first coating retainers having a first volume, each of the plurality of second coating retainers having a second volume, the first volume of the first coating retainers being greater than the second volume of the second coating retainers.

4. The stent of statement 1, each of the plurality of first coating retainers having a first volume, each of the plurality of second coating retainers having a second volume, the first volume being equal to the second volume, each of the plurality of first coating retainers having a first volume of first therapeutic agent, each of the plurality of second coating retainers having a second volume, the first volume of first therapeutic agent greater than the second volume of second therapeutic agent.

5. The stent of statement 1, the first therapeutic agent eluting from the first coating retainers at a first elution rate, the second therapeutic agent eluting from the second coating retainers at a second elution rate, the first elution rate being different than the second elution rate.

6. The stent of statement 1, the plurality of first coating retainers being formed at least partially within the body of a plurality of the members comprising the first region of the stent.

7. The stent of statement 6, the plurality of second coating retainers being formed at least partially within the body of a plurality of the members comprising the second region of the stent.

8. The stent of statement 1, wherein the first region is selected from at least one member of the group consisting of the luminal side, the abluminal side, the proximal region, the distal region, the middle region, the main body of a bifurcated stent, the contralateral region, the side branch of a bifurcated stent, members forming the side branch, the perimeter member and any combination thereof.

9. The stent of statement 8, wherein the second region is selected from at least one member of the group consisting of the luminal side, the abluminal side, the proximal region, the distal region, the middle region, the main body of a bifurcated stent, the contralateral region, the side branch of a bifurcated stent, members forming the side branch, the perimeter member and any combination thereof, the second region being different than the first region.

10. The stent of statement 1, further comprising a third region, the third region comprising a plurality of third coating retainers, the third region having a third density of third coating retainers, the third region eluting a third total volume of third therapeutic agent from the third coating retainers, wherein the density of the third coating retainers is different than the first and second densities and the third total volume of therapeutic agent is different than the first and second total volumes of therapeutic agent.

11. The stent of statement 10, wherein the third region is selected from at least one member of the group consisting of the luminal side, the abluminal side, the proximal region, the distal region, the middle region, the main body of a bifurcated stent, the contralateral region, the side branch of a bifurcated stent, members forming the side branch, the perimeter member and any combination thereof, the third region being different than both the first and second regions.

The inventive stents 10 may be made from any suitable biocompatible materials including one or more polymers, one or more metals or combinations of polymer(s) and metal(s). Examples of suitable materials include biodegradable or bioabsorbable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate. A more extensive list of therapeutic agents can be found in commonly assigned U.S. Patent Application Publication 2006/0045901, entitled Stents with Drug Eluting Coatings, hereby incorporated in its entirety.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent having a body comprising a plurality of members, the plurality of members including struts and connectors, the body comprising:
   a first region, the first region comprising a first plurality of struts arranged in a plurality of circumferential bands, longitudinally adjacent bands being engaged by connectors, each strut defining a first plurality of coating retainers, all of the coating retainers defined by a strut being arranged in a first density, each coating retainer having a depth, width, and length and having a first volume, each first coating retainer having a first volume of a first therapeutic agent, the first volume of first therapeutic agent equal to the first volume of the coating retainers, the first plurality of coating retainers eluting a first total volume of a first therapeutic agent; and
   a second region longitudinally adjacent to the first region, the second region comprising a second plurality of struts arranged in a plurality of circumferential bands, longitudinally adjacent bands being engaged by connectors, each strut defining a second plurality of coating retainers, all of the coating retainers defined by a strut being arranged in a second density, each coating retainer having a depth, width, and length and having a second volume, each coating retainer having a second volume of a second therapeutic agent, the second volume of second therapeutic agent equal to the second volume of the second coating retainers, the plurality of second coating retainers eluting a second total volume of a second therapeutic agent; and
   a side branch, the side branch in an expanded state extending at an angle to the body of the stent, the side branch comprising a third plurality of struts, each strut defining a plurality of coating retainers, all of the coating retainers defined by a strut being arranged in a third density, each coating retainer having a depth, width, and length;
   wherein the first density is greater than the second density and the second density is greater than the third density, the first total volume of therapeutic agent is greater than the second total volume of therapeutic agent, and the first volume of each of the first plurality of coating retainers is greater than the second volume each of the second plurality of coating retainers.

2. The stent of claim 1, each of the plurality of members having a width and a length, the width being substantially constant along the length of the member.

3. The stent of claim 1, each of the plurality of members having a thickness and a length, the thickness being substantially constant along the length of the member.

4. The stent of claim 1, the first plurality of coating retainers greater than the second plurality of coating retainers.

5. The stent of claim 1, the first therapeutic agent being different than the second therapeutic agent.

6. The stent of claim 1, the first volume being determined by a first length, a first width and a first depth and the second volume being determined by a second length, a second width and a second depth, wherein at least one of the first length, the first width and the first depth is different from at least one of the second length, the second width and the second depth.

7. A bifurcated stent, the bifurcated stent having a tubular body comprising a plurality of members, the plurality of members comprising a plurality of struts and connectors, the tubular body comprising:
a first region, the first region having a first plurality of struts, the plurality of struts connected one to another by turns and arranged in circumferential bands adjacent circumferential bands engaged by connectors, each strut defining a first plurality of coating retainers, all of the coating retainers defined by a strut being arranged in a first density and eluting a first local concentration of therapeutic agent, the each coating retainer having a first size; and
a second region longitudinally adjacent to the first region, the second region having a second plurality of struts and a side branch,
the second plurality of struts connected one to another by turns and arranged in circumferential bands, adjacent circumferential bands engaged by connectors, each strut defining a second plurality of coating retainers, all of the coating retainers defined by a strut being arranged in a second density and eluting a second local concentration of therapeutic agent, each coating retainer having a second size,
the side branch comprising a plurality of struts, the plurality of struts extending at an angle to the tubular body of the bifurcated stent when the side branch is in an expanded state;
wherein the first density is greater than the second density, the first local concentration is greater than the second local concentration, and the first size is equal to the second size.

8. A bifurcated stent having a tubular body comprising a first section, a second section, and a third section, the first section forming a first end region of the bifurcated stent and the third section forming a second end region of the bifurcated stent,
the first section comprising a plurality of struts engaged one to another by turns, each strut defining a first number of coating retainers, all of the coating retainers defined by a strut have a first density, the plurality of struts arranged in circumferential bands, adjacent circumferential bands being engaged one to another by connectors;
the second section comprising a plurality of struts engaged one to another by turns, each strut defining a second number of coating retainers, all of the coating retainers defined by a strut have a second density, the second section further comprising a side branch,
the side branch extending at an angle to the tubular body of the bifurcated stent when the side branch is in an expanded state, the side branch comprising a plurality of struts, each strut defining a third number of coating retainers, all of the coating retainers defined by a strut have a third density;
the third section comprising a plurality of struts engaged one to another by turns, each strut defining a fourth number of coating retainers, all of the coating retainers defined by a strut have a fourth density, the plurality of struts arranged in circumferential bands, adjacent circumferential bands being engaged one to another by connectors;
wherein the first number of coating retainers and the fourth number of coating retainers are the same, wherein the first density and the fourth density are the same, and wherein the third number of coating retainers is different than the first number of coating retainers.

9. The stent of claim 8, wherein the second density is the same as the first and fourth densities.

10. The stent of claim 9, wherein each strut has a length, the struts of third section having a shorter length than the struts of the first, second, and fourth sections.

11. The stent of claim 8, wherein the second number of coating retainers is the same as the first number of coating retainers.

12. The stent of claim 8, wherein the second density is two times greater than the first density and two times greater than the fourth density.

13. The stent of claim 8, wherein the second density is less than the first and fourth densities and greater than the third density.

14. The stent of claim 8, wherein the second number of coating retainers is different than the first number of coating retainers.

15. The stent of claim 8, the second section further comprising a perimeter member, at least some of the plurality of struts of the side branch being engaged to the perimeter member and some of the plurality of struts of the second region being engaged to the perimeter member, the perimeter member defining a fifth number of coating retainers, the fifth number being greater than the first, second, third, and fourth numbers of coating retainers.

16. The stent of claim 15, the perimeter member being engaged to a circumferential band of the first section by a connector and being engaged to a circumferential band of the second section by a connector.

17. The stent of claim 15, the first section and the fourth section having the same number of struts.

18. The stent of claim 8, wherein each turn has a first width and each strut has a second width greater than the first width.

19. The stent of claim 18, wherein each connector has a third width substantially equal to the first width.

* * * * *